(12) United States Patent
Cleveland et al.

(10) Patent No.: US 12,241,896 B2
(45) Date of Patent: ***Mar. 4, 2025

(54) PROTEOMIC ASSAY USING QUANTUM SENSORS

(71) Applicant: SomaLogic Operating Co., Inc., Boulder, CO (US)

(72) Inventors: Jason Paul Cleveland, Boulder, CO (US); Karoly Holczer, Los Angeles, CA (US); Barry Patrick John Vant-Hull, Boulder, CO (US)

(73) Assignee: SomaLogic Operating Co., Inc., Boulder, CO (US)

( * ) Notice: Subject to any disclaimer, the term of this patent is extended or adjusted under 35 U.S.C. 154(b) by 13 days.

This patent is subject to a terminal disclaimer.

(21) Appl. No.: 18/350,379

(22) Filed: Jul. 11, 2023

(65) Prior Publication Data
US 2023/0349896 A1 Nov. 2, 2023

Related U.S. Application Data

(63) Continuation of application No. 17/672,089, filed on Feb. 15, 2022, now Pat. No. 11,698,373, which is a
(Continued)

(51) Int. Cl.
*G01N 33/543* (2006.01)
*G01N 21/64* (2006.01)
(Continued)

(52) U.S. Cl.
CPC ....... *G01N 33/54386* (2013.01); *G01N 21/64* (2013.01); *G01N 21/78* (2013.01);
(Continued)

(58) Field of Classification Search
CPC .. G01N 33/54386; G01N 21/64; G01N 21/78; G01N 24/088; G01N 33/487; G01N 33/5308; G01N 33/54306; G01N 33/6803; G01N 21/6489; G01N 2021/6495; G01N 2021/7783; G01N 2570/00;
(Continued)

(56) References Cited

U.S. PATENT DOCUMENTS 10,481,155 B2 * 11/2019 Cleveland ............ G01N 24/088
11,249,080 B2 * 2/2022 Cleveland .............. G01N 21/78
(Continued)

FOREIGN PATENT DOCUMENTS

CN 104870365 A 8/2015

*Primary Examiner* — Dennis White
(74) *Attorney, Agent, or Firm* — Kolitch Romano Dascenzo Gates LLC

(57) ABSTRACT

Apparatus and methods for the detection of proteins in biological fluids such as urine using a label-free assay is described. Specific proteins are detected by their binding to highly specific capture reagents such as SOMAmers that are attached to the surface of a substrate. Changes to these capture reagents and their local environment upon protein binding modify the behavior of color centers (e.g., fluorescence, ionization state, spin state, etc.) embedded in the substrate beneath the bound capture reagents. These changes can be read out, for example, optically or electrically, for an individual color center or as an average response of many color centers.

20 Claims, 9 Drawing Sheets

Related U.S. Application Data continuation of application No. 16/686,911, filed on Nov. 18, 2019, now Pat. No. 11,249,080, which is a continuation of application No. 15/917,524, filed on Mar. 9, 2018, now Pat. No. 10,481,155.

(51) Int. Cl.

| | |
|---|---|
| *G01N 21/77* | (2006.01) |
| *G01N 21/78* | (2006.01) |
| *G01N 24/08* | (2006.01) |
| *G01N 33/487* | (2006.01) |
| *G01N 33/53* | (2006.01) |
| *G01N 33/68* | (2006.01) |
| *G01R 33/32* | (2006.01) |

(52) U.S. Cl.
CPC ......... *G01N 24/088* (2013.01); *G01N 33/487* (2013.01); *G01N 33/5308* (2013.01); *G01N 33/54306* (2013.01); *G01N 33/6803* (2013.01); *G01R 33/323* (2013.01); *G01N 21/6489* (2013.01); *G01N 2021/6495* (2013.01); *G01N 2021/7783* (2013.01); *G01N 2570/00* (2013.01)

(58) Field of Classification Search
CPC ............. G01N 33/54373; G01N 24/10; G01N 33/588; G01N 33/68; G01N 33/543; G01N 33/551; G01N 33/54333; G01N 33/54366; G01N 33/6842; G01R 33/323; C12Q 1/6834

See application file for complete search history.

(56) References Cited

U.S. PATENT DOCUMENTS

| | | | |
|---|---|---|---|
| 11,698,373 B2 * | 7/2023 | Cleveland | G01N 33/6803 422/82.08 |
| 2011/0062957 A1 * | 3/2011 | Fu | G01N 24/088 324/307 |
| 2015/0192596 A1 | 7/2015 | Englund et al. | |
| 2015/0377865 A1 | 12/2015 | Acosta et al. | |

\* cited by examiner

PROTEOMIC ASSAY USING QUANTUM SENSORS

FIELD

The present invention relates to the simultaneous detection of hundreds or thousands of proteins in biological fluids such as blood or urine, a first step in proteomic analysis. In particular, the present invention achieves such detection without resorting to mass spectrometry or chromatographic methods, and utilizes a label-free assay, allowing for instrumentation that is compact, inexpensive, and reusable.

INTRODUCTION

Conventionally, various attempts to evaluate genetic activity or decode biological processes, including disease process or a biological process of pharmacological effect, have been focused on genomics. However, proteomics can provide further information about the biological function of cells and organisms. Proteomics includes qualitative and quantitative measurement of gene activity by detecting and quantifying the expression on a protein level rather than the genetic level. Proteomics also includes a study of events which are not coded genetically, such as a post-translational modification of proteins and interactions between proteins.

At present, it is possible to obtain an enormous volume of genome information. DNA chips have come into practical use as molecular arrays for this purpose and the price of direct DNA sequencing has continued to drop significantly. Likewise, there is an increasing demand for high throughput proteomics. In order to detect proteins, which are more complicated and more variable in biological functions than DNA, there are proposed protein chips, which are currently the subject of intense study for many applications. Proteomics is far preferable to genomics for the monitoring of health, as the genome is static, indicating only medical potential, while the proteome varies dynamically with a patient's medical state, and may even be said to define their medical state. However, detecting and quantitating proteins is hard, while detecting and quantitating nucleic acids is relatively easy. This has motivated many efforts to measure mRNA (messenger RNA) concentrations as a proxy for protein concentrations. Unfortunately, mRNA concentrations have been shown not to correlate well with protein concentrations. It appears that proteomics necessarily relies on the ability to detect proteins directly.

"Protein chip" is a collective term used to refer to any device in which protein or a molecule for catching such a protein (a capture reagent) is fixed on a surface of a chip, allowing for the detection of protein binding. Until recently, the capture reagents on protein chips were overwhelmingly antibodies. Detection of specific proteins in complex mixtures such as biological fluids demands high specificity, so many protein chips utilizing antibodies also depend on sandwich assays in order to boost specificity. Such assays are known to have significant shortcomings for proteomics, some of which are protein and/or antibody specific and some of which are specific to sandwich assays.

At present, there is no economically viable means by which proteomic data may be collected from human subjects on a routine basis. Proteomic measurement of samples is usually accomplished by various chromatographic techniques for sample preparation combined with various mass spectrographic techniques for detection and quantification. The instruments used for these procedures are both costly and bulky, so that samples usually must be shipped to a central processing facility. The need for sample transport requires that samples be processed at the point of collection for storage during shipping, or stored on site until transport is available. Unfortunately, preparation and storage protocols tend to vary widely across sites, and even within the same sites. Differences in these protocols invariably lead to significant variation in the downstream proteomic measurements, rendering analysis difficult or impossible.

An ideal proteomic collection device would minimize cost by approaching fully solid-state operation (few moving parts), utilizing label-free detection techniques so that reagent use would be minimal, would be reusable for an indefinite number of measurement runs, and would operate on a small volume of biological fluid. Variations in sample analysis due to variation in sample preparation and storage protocols could be reduced by minimizing or eliminating sample preparation, and by performing sample measurement at the place and time and collection, eliminating sample storage and transport.

A new class of non-protein-based capture reagents is found in nucleic acid molecules. The dogma for many years was that nucleic acids had primarily an informational role. Through a method known as "Systematic Evolution of Ligands by EXponential enrichment," sometimes termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", U.S. Pat. No. 5,270,163 (see also WO91/19813) entitled "Nucleic Acid Ligands" each of which is hereby incorporated by reference into the present disclosure. Each of these publications, collectively referred to herein as the SELEX patent applications, describes a method for making a nucleic acid capture reagent to any desired target molecule.

The SELEX process provides a class of products which are referred to as nucleic acid ligands or aptamers, each having a unique sequence, and having the property of binding specifically to a desired target compound or molecule. Each SELEX-identified nucleic acid capture reagent is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

SOMAmers (Slow Off-rate Modified Aptamers) are aptamers having improved off-rate characteristics. This improved off-rate characteristic may be represented as a rate of dissociation ($t_{1/2}$) or the point at which 50% of the aptamer/target complex has dissociated. Such rates of dissociation may vary, generally, from greater than 5, 10, 15, 20, 30, 40, 50, 60, 70, 80, 90, 100, 120, 140, 160, 180, 200, 220 and 240 minutes, this being the average time it takes a protein-aptamer complex to dissociate. In addition, SOMAmers contain modified nucleosides that provide for different built-in functionalities. These functionalities may include tags for immobilization, labels for detection, means to promote or control separation, hydrophobic sidechains to provide better affinity with proteins, etc. The modifications to improve affinity with proteins are chemical groups that are attached to the 5-position of the pyrimidine bases. By functionalizing the 5-position (e.g with a benzyl, napthyl or indole group) the chemical diversity of the SOMAmers is expanded, allowing high affinity binding with a wider range of target molecules. Additionally, some polymerases are still able to transcribe DNA with modifications in these positions, thus allowing the amplification necessary for the SELEX process. SOMAmers, and the methods to produce them, are described in U.S. Pat. Nos. 7,964,356 and 7,947,447, both entitled "Method for generating aptamers with improved off-rates," each of which is hereby incorporated by reference into the present disclosure.

It should be noted that while aptamers and SOMAmers may be discovered by the SELEX process there may be other means to select them. For example, as computer modeling of molecular interactions improve, it may become possible to directly calculate an ideal nucleic acid sequence for an aptamer and the associated chemical modifications for a SOMAmer to generate capture reagents specific to a given target molecule. Other chemical techniques for screening for aptamers and SOMAmers besides SELEX are also possible.

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands" see also, e.g., U.S. Pat. Nos. 6,242,246, 6,458,543, and 6,503,715, each of which is entitled "Nucleic Acid Ligand Diagnostic Biochip". These patents are hereby incorporated by reference into the present disclosure. Once the microarray is contacted with a sample, the aptamers bind to their respective target molecules present in the sample and thereby enable a determination of the absence, presence, amount, and/or concentration of the target molecules in the sample.

Label-free assays are considered to be highly desirable, but are not always achievable. A label is any foreign molecule that is chemically or temporarily attached to the molecule of interest to detect molecular presence or activity. Label-free assays utilize molecular biophysical properties such as molecular weight, molecular charge, dielectric constant, or (in the case of the present invention) affinity for an aptamer to monitor molecular presence or activity. Some embodiments of the invention utilize a spin label linked to an aptamer attached to a surface. Because this spin label is attached to a component of the detection system (e.g., an aptamer) as opposed to the molecule of interest (e.g., a protein), the present invention is considered to be a label-free assay. Many sensitive assays require that the analyte be "labeled" with a detectable tag. This tag, or label, could be a dye, a radio-isotope, or anything else that is easily measured, thereby measuring the analyte by proxy.

The ELISA assay (Enzyme-Linked ImmunoSorbent Assay) has been considered the "gold standard" of immunoassays due to its high sensitivity and specificity, but is not considered to be label free. ELISA uses two antibodies specific for different binding points (epitopes) on the analyte, making it a "sandwich assay" as opposed to label-free. One antibody is immobilized to a surface, and captures the analyte from the sample fluid. The second antibody is linked to an enzyme that catalyzes a detectable change in a specific additive. After the analyte is captured by the immobilized antibody, the surface is washed to remove non-desired molecules, and the second antibody is added, followed by a wash, and addition of the additive, which is usually catalyzed into a detectable dye. Although the second antibody adds both specificity and detectability, it also requires several steps involving costly reagents. A label-free form of the assay would be comprised of only the first antibody, and some means of detecting the binding of the analyte.

SUMMARY

Biochips, including protein chips, require a means of detecting the analytes in a sample for which they are specific, while disregarding other molecules. The detection apparatus and methods described by the present teachings are based on color centers located close to the surface of a solid that can be probed via Optically Detected Magnetic Resonance (ODMR) or other techniques. Color centers are point defects in otherwise close to ideal, transparent, crystalline insulators or large band-gap semiconductors such as diamond, silicon carbide, or silica. They can consist of substitution defects where an atom in the crystal is replaced by an atom of another type, vacancy defects where an atom is missing, or combinations of the two.

Color centers have localized electron orbitals that are analogous to those of a free atom. The electronic states are ordered in terms of principal orbital and magnetic quantum numbers and can be stable when charged, neutral, or both. The wide band-gap or insulating crystal that surrounds the color center plays the role of "vacuum" separating the color centers. At low enough density, this results in independent "atom-like" entities with a rich, well-resolved, complex energy spectrum with discrete optical transitions in the visible range (hence the name "color center") that co-exist with electronic and/or nuclear spin states with long relaxation times.

Of particular interest are color centers whose fluorescence intensity depends on the spin polarization state (i.e. the magnetic quantum number of the ground state). In this case the magnetic sublevel population is reflected in the fluorescence intensity, allowing for optical detection of magnetic resonance. Because ODMR essentially transforms what would be detection of radio frequency (RF) or microwave frequency quanta due to transitions in the magnetic sublevels into detection of a much higher energy optical photon, it has a distinct advantage in sensitivity (about 5 orders of magnitude) and for strong fluorescence, allows optical observation of individual color centers.

An example of such a color center capable of ODMR is the nitrogen-vacancy (NV) center in diamond crystals. Although the preferred embodiment described in the present invention would utilize NV centers in diamond for detection, the invention can also use other color centers. Diamond itself has over 500 known color centers, most associated with nitrogen. Other elements known as possible substitutions in the diamond lattice include nickel, boron, silicon, hydrogen, and cobalt. Color centers in other crystalline lattices include, for example, Germanium-related defects in germanosilicate glass, Silicon vacancies in silicon carbide, and X-ray induced defects in $LiBaF_3$ crystals.

As the name implies, the NV center consists of a nitrogen substitution for a carbon atom situated next to a neighboring vacancy in the lattice. This is shown in FIG. 1, which is a schematic depiction of a diamond crystal, generally indicated at 100, including an NV center indicated at 104. The NV center is a paramagnetic color center with unique coupling between its electronic spin states and optical states. It is capable of emitting intense and stable fluorescence (i.e. large absorption coefficient combined with short lifetime of the excited state) and also exhibits very long magnetic relaxation times, making it a sensitive detector of local properties such as the magnetic or electric fields. Diamond itself is exceedingly stable mechanically, thermally, and chemically. At the same time, the diamond surface is amenable to chemical modification, which is useful for attaching molecular agents. Pure diamonds are optically clear, allowing unfettered excitation and emission of fluorescent centers, and the fluorescence also exhibits no photobleaching and minimal luminescent intermittency ("blinking"). The combination of all these qualities make NV centers a good candidate for very sensitive biosensing.

The present disclosure describes devices, systems and methods for detecting target molecules in a sample, based on a change in a property of one or more color sensors disposed near the surface of a substrate, when a target molecule binds to a capture reagent attached to the surface. A detector can be configured to detect the change in the color center property, thereby detecting the target molecule in the sample. In some cases, the target molecule is a protein, and the capture reagents are aptamers. In some cases, the color centers are NV centers disposed in diamond, and the change in property is a change in fluorescence emission. In some cases, a large number of protein species may be targeted in one assay, such as hundreds, thousands, tens of thousands or even more.

The present teachings involve the attachment of aptamers or SOMAmers on a surface, such as a diamond surface, as well as passivation of the regions of the surface not bound with aptamers or SOMAmers against non-specific binding by undesired proteins. The present teachings also involve regeneration of aptamers or SOMAmers attached to a surface for further rounds of protein detection.

The present teachings aim to eliminate all moving parts aside from those related to bulk delivery of fluids to the active surface of the biochip. These fluids include the sample fluid, wash fluids, and fluids used for regeneration of the biochip. The proposed scheme for detection is a label-free method, meaning that no detection agents need to be added to the sample to enable the measurement of the proteins of interest. Regeneration of the active surface is non-destructive, requiring only a mild buffer wash to dissociate the protein from the aptamer or SOMAmer. NV centers are extremely stable and aptamers and SOMAmers themselves are highly stable, allowing for hundreds of uses.

More specifically, once the sample fluid has contacted the active surface, some amount of time must be allowed for the proteins to bind the immobilized aptamers. This binding time should also include time necessary for the proteins to diffuse from the bulk fluid to the surface, which may take hours. During this binding time, the sample fluid may be static, but it is more common to agitate or recirculate the fluid in order to bring unbound proteins closer to the surface and thereby reduce the distance they need to diffuse. After the binding step has been completed, it is common to wash the surface to remove unbound proteins. This wash is commonly performed with buffer solutions similar to the sample fluid, such as phosphate buffered saline, or with distilled water. When high specificity detection is required, the washes may be harsher, using higher salt concentrations, mild denaturants such as low concentration (<1 M) urea, or including competitors to the protein of interest. Such competitors may be general, such as albumin, which competes with protein, or heparin, which competes with nucleic acids. Various bulk forms of nucleic acid can be used as well, such as salmon-sperm DNA, or bulk synthesized random DNA. The competitors may also be specific, such as the use of similar proteins to the protein of interest, or non-human proteins to compete with human proteins. As with binding, the wash fluid may be static or agitated, and some time must be allowed for diffusion from the surface into the bulk fluid.

The present teachings eliminate most variance in sample analysis by performing the assay and analysis at the point of collection, for example, inside the test subject's toilet. Assaying and analyzing fresh urine within the collection receptacle (namely, the toilet) eliminates the need to store and transport the samples, along with the associated variance.

The ability to perform routine proteomics cheaply at the level of the consumer would have profound effects on science and healthcare. Proteomic science lags far behind its potential due to the simple lack of the large number of quality samples necessary for meaningful analysis. The present teachings greatly ease both the collection and the analysis of such samples. Better proteomic science leads to better medical diagnostic predictions. However, such diagnostic predictions are of little utility in healthcare without ease of sample collection from patients and ease of analysis. Thus, having provided for better proteomic science, the present teachings will also provide for easier application of that science in healthcare.

Various other features of systems and methods according to the present teachings are described in this disclosure. Features, functions, and advantages may be achieved independently in various embodiments of the present disclosure, or may be combined in yet other embodiments, further details of which can be seen with reference to the following description and drawings.

DESCRIPTION

Figure 1:
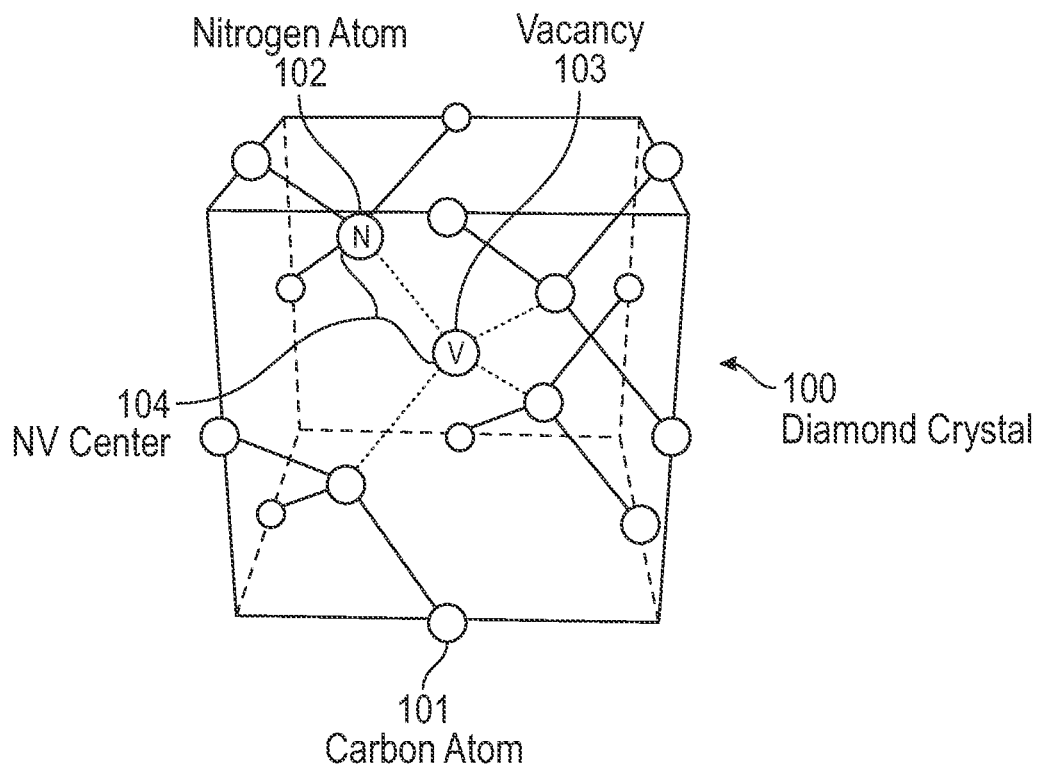
FIG. 1 is a schematic diagram depicting a nitrogen vacancy center in diamond.

FIG. 1 is a schematic diagram depicting a nitrogen vacancy center in diamond. In its pure form, a diamond crystal 100 would consist solely of carbon atoms 101. When a nitrogen atom 102 substitutes for a carbon atom in the diamond crystal, and is located adjacent to a vacancy 103 in the crystal, a nitrogen-vacancy center 104 is created.

As can be seen in FIG. 1, since each carbon has four identical bonding partners, there are four crystallographic directions upon which the axis of the NV center can lie depending on how the vacancy is placed relative to the nitrogen substitution. These are the [111], [1$\bar{1}$1], [$\bar{1}$1$\bar{1}$], [$\bar{1}\bar{1}$1] directions. Additionally, in any given direction, the order of the nitrogen substitution and vacancy can be reversed so there are, in fact, eight unique NV center configurations.

The interactions of a molecule with the NV center depend not only on the distance to the NV center but also on the relative orientation of the two. Additionally, there are optimal directions for the excitation and detected light. All of these considerations must be taken into account when choosing which face of the diamond crystal should be used as the detecting surface.

Nitrogen-vacancy centers may be embedded in a crystalline structure, such as a diamond, at the desired depth by introducing the nitrogen impurities and the vacancies at the desired depth, then annealing from 1000K-1300K, which allows the vacancies to collocate via diffusion to the nitrogen impurities. Nitrogen defects may be implanted at the desired depth either through a nitrogen pulse during chemical vapor deposition (CVD) of the diamond matrix or by ion beam implantation after the deposition has completed. Vacancies are implanted or created via ion beams of e– [54], $H_+$ [55] or $He_+$.

Because natural diamond contains about 1% $^{13}C$, which has a ½ nuclear spin (it is a nuclear paramagnet) and therefore interacts with NV centers, the relaxation times of NV centers can be increased by growing an overlayer of isotopically pure $^{12}C$ diamond on an existing crystal using CVD and creating NV centers within this layer. Similarly, the ½ nuclear spin of $^{15}N$ is preferred over the nuclear spin 1 of the $^{14}N$ isotope. Also, as the nitrogen substitutions carry a spin, the larger the percentage of nitrogens that can be converted to NV centers the cleaner the sample will be from a magnetic perspective.

Under the proper CVD conditions, the orientation of NV centers created can be highly biased. That is, rather than all 8 possible orientations being equally populated, a single orientation can occur preferentially over the others. Alignments as high as 99% may be possible. This can be very useful for creating a device where all of the NV centers are identical and optimally oriented. For example, if the sensing surface of the diamond is a (111) plane, and the great majority of NV centers can be oriented along the [111] direction, they will all be oriented perpendicular to the sensing surface.

For some embodiments of the present teachings, it is desirable to create a very thin layer of diamond attached to another substrate, such as silicon, where additional detection electronics exist. Another use for ion implantation is to insert a "break layer" at a certain depth in a thick diamond crystal using, for example, hydrogen atoms. After bonding the thick diamond crystal to the other substrate, the diamond can be mechanically shocked and will fracture along the break layer leaving behind a thin layer of diamond crystal. Similar techniques are used in the semiconductor industry already.

Figure 2:
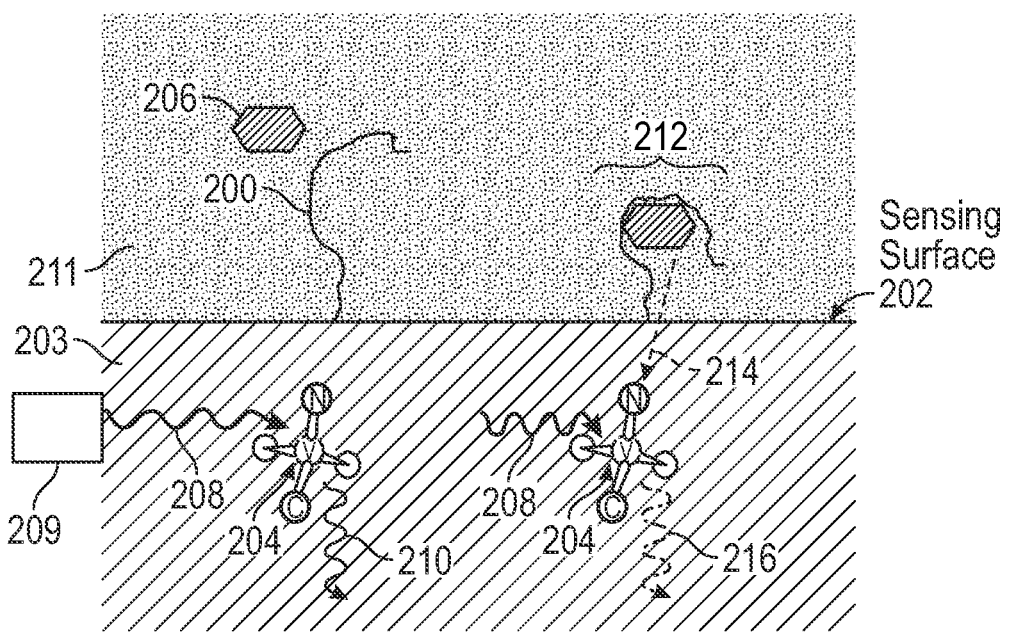
FIG. 2 is a schematic depiction of target molecule detection, according to aspects of the present teachings.

FIG. 2 is a schematic depiction of target molecule detection, according to aspects of the present teachings. A capture reagent 200 is attached to the surface 202 of a substrate 203 (e.g., a high-purity insulator such as a crystalline film, a diamond film, and/or a single-crystal diamond) in close proximity to a color center 204. When the color center is irradiated with excitation light 208 (e.g., from optical source 209), it is stimulated to emit fluorescent light 210, characterized by a spectrum and intensity. Capture reagent 200 is contacted with a sample fluid 211 (e.g., by exposing surface 202 to the sample fluid) such that a target analyte 206 (also called a target molecule) in the sample solution binds to the capture reagent 200 to form a complex 212, thereby causing and/or changing an interaction 214 with the color center, which produces a detectable change in properties (e.g., intensity) of the emitted fluorescent light 216. In interaction 214, the color center may detect electric field changes or magnetic field changes upon binding of a target molecule to a capture reagent. A property of the color center (e.g., a property associated with a magnetic resonance or spin of the color center) be changed by interaction 214.

The sample fluid may be a biological fluid. Capture reagent 200 may be a nucleic acid molecule, an oligonucleotide, an aptamer, a SOMAmer, or any other binding agent configured to bind to a target molecule. In some examples, the capture reagent includes at least one 5-position-modified pyrimidine (i.e., a pyrimidine, such as a uridine or a cytidine, having a modified 5-position). In some examples, different types of 5-position-modified pyrimidines are attached to the surface. For example, at least one 5-position-modified uridine and at least one 5-position-modified cytidine may be attached to the surface.

The target analytes may be a protein. Proteins include normally folded polypeptide chains, abnormally folded polypeptide chains, unfolded polypeptide chains, fragments of a polypeptide chain that may or may not be normally folded, short polypeptides, polypeptides that incorporate non-natural amino acids, and polypeptides that are post-translationally modified (e.g., phosphorylation, glycosylation, disulphide bonding, etc.) or polypeptides assembled into a protein complex. The target analytes may also include small molecules found in biological fluids such as metabolites.

Figure 3A:
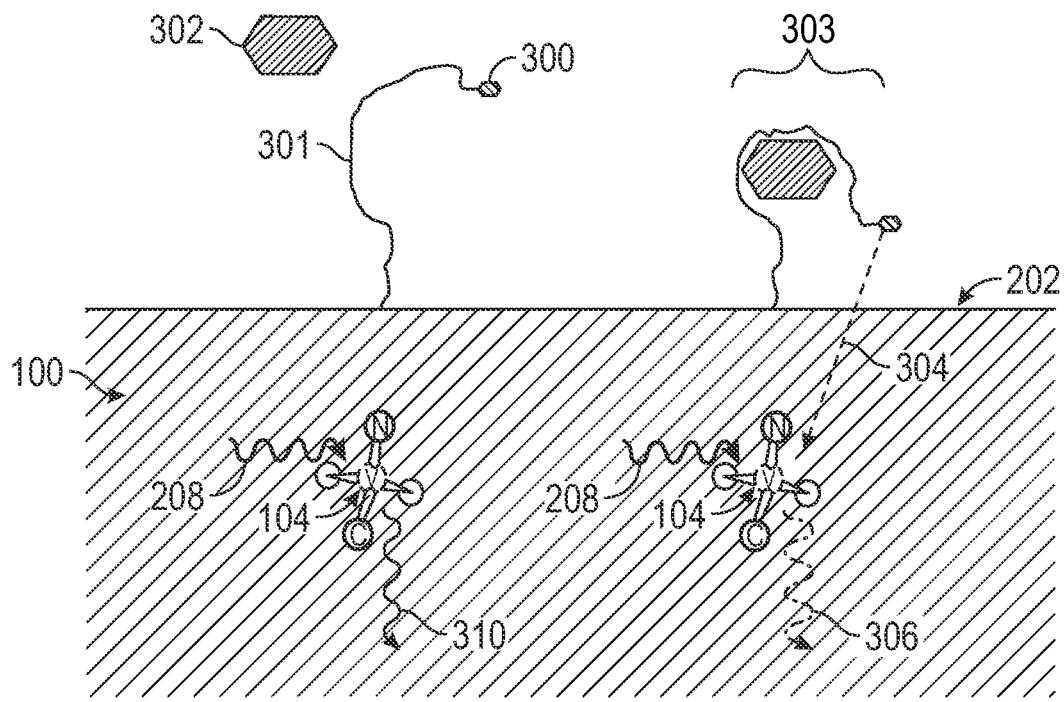
FIG. 3A is a schematic depiction of an interaction mechanism that may be used to detect target molecules, according to aspects of the present teachings.
Figure 3B:
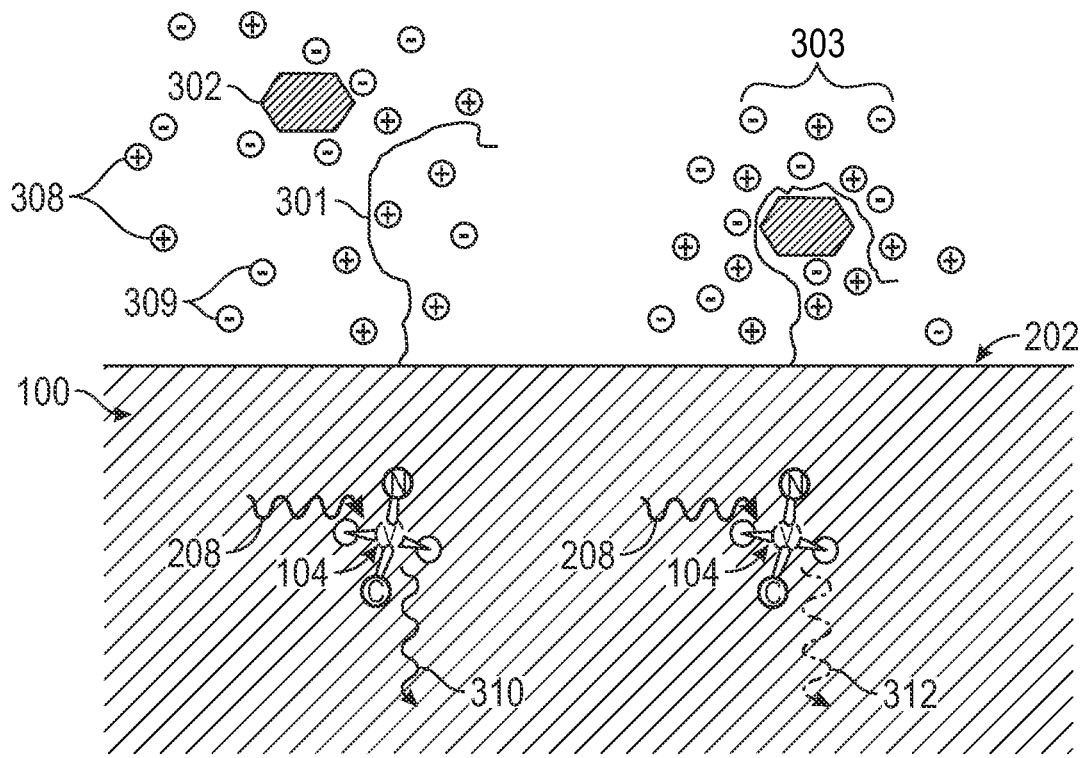
FIG. 3B is a schematic depiction of another interaction mechanism that may be used to detect target molecules, according to aspects of the present teachings.

FIGS. 3A-3B are schematic depictions of two possible interaction mechanisms of the detection technique where the color centers are NV centers, the target analytes are proteins, and the capture reagents are aptamers.

FIG. 3A is a schematic depiction of an interaction mechanism that may be used to detect target molecules utilizing magnetic spin labels, according to aspects of the present teachings. Stable organic molecules are typically diamagnetic, the paramagnetic molecules (i.e. "free radicals") possess unpaired electrons, therefore they are chemically active, and prone to lose their spin through chemical reactions. Stable free radicals that survive exposure to a bio-chemical environment are exceptional. Spin-labels are stable paramagnetic organic molecules or complexes that are capable of binding to another molecule, particularly to nucleic acids and amino acids, specifically developed for site-directed spin-labeling of large bio-molecules.

The spin labels most often used are nitroxide-containing small organic molecules, or metal chelators such as EDTA that complex with high affinity to paramagnetic metal ions, developed for incorporation into nucleic acids. Nitroxide derivatives of nucleic acid bases have also been developed. Recently, triarylmethyl (Trityl) radical derivatives have also become popular for labeling both proteins and nucleic acids. EDTA derivatives of both deoxyribo-thymine and deoxyribo-cytosine have been developed in phosphoramidite form for use in DNA synthesizers. For measurements where the spin label is intended to simply change the relaxation time of NV center, all that is important is that a magnetic interaction exists and a wide variety of spin labels are applicable. However, for measurements where the spin states of the label are directly addressed, the individual spectra of the spin label becomes relevant. For example, in DEER, the narrower the spectrum and the longer the lifetime of the spin label, the better. As a specific example, in DEER the triplet splitting of the spectrum due to hyperfine coupling to the $^{14}$N is a handicap, and the single line spectrum of deuterated Trityl is a preferred choice.

In FIG. 3A, an aptamer 301 linked to a magnetic spin label 300 is attached to the sensing surface 202 of a diamond crystal 100, in close proximity to a color center 104. A target protein 302 in the sample solution binds to the aptamer to form a complex 303, changing the proximal relationship of the spin label with the NV center which affects the interaction 304 between the spin label and the NV center, thereby producing a detectable change in fluorescent properties 306 of the NV center.

More specifically, FIG. 3A illustrates a specific configuration designed to maximize the magnetic interaction by placing a spin-labeled aptamer in the proximity of an NV center in diamond. The conformational change upon binding of the protein can move the spin label relative to the NV center. A movement closer to the NV center will increase the magnetic field at the NV center resulting in a measurable change in the dynamic or quasi-static characteristics of the NV center sublevel spectrum.

The sublevel spectrum may be probed using a detector assembly configured to irradiate the NV center with excitation light and to detect emission of electromagnetic radiation from the NV center. The detector assembly may detect changes in the sublevel spectrum by irradiating the NV center with microwave radiation over a range of frequencies including a resonant frequency of the sublevels, and detecting changes in the radiation emitted by the NV center. Radiation at the resonant frequency may induce conversion of ground-state electrons in the NV center from a first sublevel to a second sublevel and thereby induce a change in a characteristic of the emitted radiation. An example characteristic of the emitted radiation is the relationship between the frequency of the excitation light and the frequency of the emitted light. Furthermore, the addition of a spin label along with microwave excitation open a variety of options to manipulate spin label interaction with the NV center.

FIG. 3B is a schematic depiction of another interaction mechanism that may be used to detect target molecules utilizing electrostatic interactions, according to aspects of the present teachings. An aptamer 301 is attached to the sensing surface 202 of a diamond crystal 100 in close proximity to an NV center 104. Both positive ions 308 and negative ions 309 are present in the fluid being analyzed. The aptamer's negatively charged backbone will attract positive ions 308. These associated ions affect the electric field local to the NV center, so that when the NV center is irradiated with excitation light 208, it is stimulated to emit fluorescent light 310, characterized by a spectrum and intensity. A protein 302 in the sample solution, also has ions associated with it according to its charge. The protein binds to the aptamer to form a complex 303, thereby changing the distribution of charge, and thus the electric field local to the NV center, thereby producing a detectable change in properties of the emitted fluorescent light 312.

More specifically, FIG. 3B illustrates a configuration where electrostatic interactions can be explored. The presence of mobile charges near the surface significantly affects the relaxation time of NV centers. There is a negative charge associated with the NV center itself and also negative charges associated with the backbone of the aptamer. Additionally, the target proteins themselves can be charged. These charges will be screened by counter-ions in the solution. Binding of a protein molecule to an aptamer will rearrange this charge distribution relative to the NV center. Furthermore, the protein molecule itself has a dielectric constant much lower than water and its presence will affect the screening of the charge distribution. Both effects will give rise to a change in the quasi-static and dynamic electric fields present at the NV center and affect the characteristics of the sublevel spectrum.

The degree to which static or dynamic changes in the sublevel spectrum dominate the interaction can be affected by the environment in which the measurement is made. If the measurements are made at room temperature, the mobility of charges in solution and the molecules themselves are expected to contribute significant dynamic changes that can be characterized by direct measurement of $T_1$. In contrast, if the measurements are made at a temperature below freezing of the biological fluid, these dynamic changes should be suppressed and allow direct detection of the static splitting in the sublevels. In the case of the spin-labeled aptamer, making the measurement in a frozen state will significantly increase the relaxation time of the spin label and allow techniques like double electron-electron resonance (DEER) to be used to measure directly the distance change between the spin label and the NV center.

The optimum configuration for the placement of the NV centers also depends on whether the changes in the spectrum are dominated by quasi-static or dynamic changes. If dynamic changes are dominant and direct $T_1$ measurements are being used, it is likely that the NV centers can be located closer to the surface and also closer to each other. On the other hand, careful measurements of quasi-static changes to the spectrum will require the high fidelity of longer relaxation times (primarily $T_1$) and hence require NV centers further from the surface and well separated from each other. The NV center distance from the surface is a compromise between maximizing the interaction with the aptamer and its binding target and preserving the long relaxation times that make the NV sensitive detectors of quasi-static electric and magnetic fields.

FIGS. 3A-3B explored two limits of interaction where the magnetic and electric fields are the dominant ones causing a change in the NV center upon binding of the analyte. Just as the SELEX process was modified to screen for slow off-rates in the creation of SOMAmers, a step can be added to later selection rounds to bind candidate aptamers to a device like those described here and measure NV center response to target binding. In this way, SOMAmers that maximize the signal contrast upon a binding event can be maximized.

Figure 4:
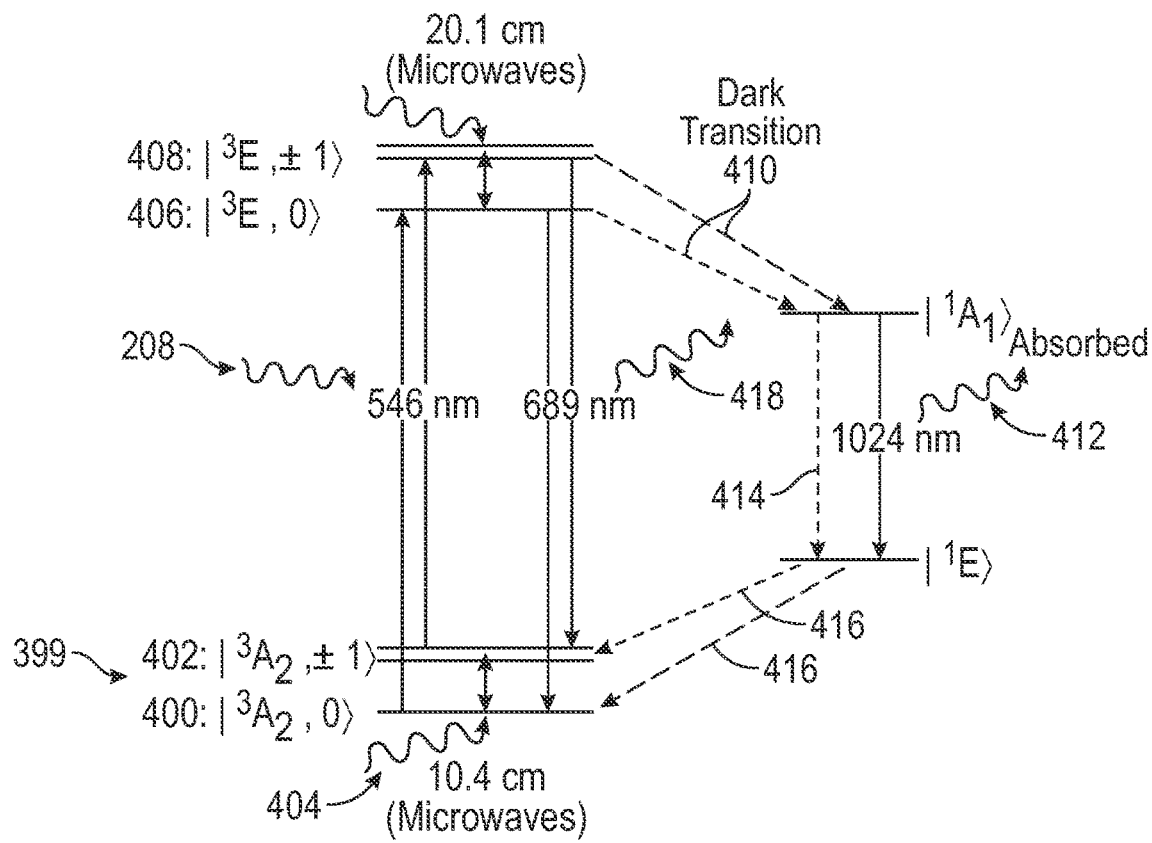
FIG. 4 is a schematic depiction of electron energy levels in a diamond nitrogen vacancy (NV) center, and the transitions between these levels, according to aspects of the present teachings.

FIG. 4 is a schematic depiction of electron energy levels in a diamond nitrogen vacancy (NV) center, and the transitions between these levels, according to aspects of the present teachings. More specifically, FIG. 4 is a simplified schematic of the electron energy levels in a negatively charged NV center in diamond and the transitions between these levels. A ground state 399 of an electron in an NV center includes three sublevels (also called substates or states). The zero-spin sublevel 400 has the lowest energy, and is designated $|^3A_2,0\rangle$. The $m_s=+1$ and $m_s=-1$ spin sublevels 402 have identical energy in the absence of external fields, and are designated $|^3A_2,\pm1\rangle$.

External fields affect the $m_s=\pm1$ spin states but not the $m_s=0$ spin states, lowering the energy of the $m_s=-1$ spin states while raising the energy of the $m_s=+1$ spin states. For instance, a 1027 Gauss magnetic field that is aligned with the symmetry axis of the NV center will lower the $|^3A_2,-1\rangle$ level to that of the $|^3A_2,0\rangle$ level at room temperature. The presence of a magnetic spin label in close proximity to the NV centers would have a similar, but much smaller effect. Irradiation with microwaves of the correct frequency 404 (e.g., a resonant frequency) will induce transitions from the ground $m_s=0$ spin state to the ground $m_s=\pm1$ spin states. Transition from the ground $m_s=0$ spin state to the excited $m_s=0$ spin state 406, designated $|^3E,0\rangle$, or from the ground $m_s=\pm1$ spin states to the excited $m_s=\pm1$ spin states 408, designated $|^3E,\pm1\rangle$, may be induced by irradiation with excitation light of the correct frequency 208.

Transitions from the excited states to their corresponding ground states are accompanied by emission of red photons 418. Alternatively, transitions from the excited states to the ground states may occur via the "dark transition" 410, so called because it most or all of the transition is accomplished without any photon emission or only with longer wavelength infrared photon emission 412. The dark transition 410 may either be accompanied by the emission of a photon 412 in the infrared range which will be absorbed by the diamond lattice, or along a path 414 with no photon emission at all. In most cases, the dark transition results in a spin transition 416 from $|^3E, \pm1\rangle$ to $|^3A_2,0\rangle$. Approximately 30% of the electrons on the $|^3E, \pm1\rangle$ level transition to the ground state via the dark transition, producing no detectable photon emission. Because of this, electrons in the $m_s=\pm1$ spin states produce only about 70% of the fluorescence of electrons in the $m_s=0$ spin state.

Even more specifically, FIG. 4 shows a schematic energy level structure consistent with the observations and calculations for a negatively charged NV center. Six electrons are located in a $C_{3V}$ symmetry (imposed by the static lattice structure) ground state "molecular orbital". These orbitals are linear combinations of the four orbitals consistent with the band structure calculation of diamond. Energetically, this ground state, labeled as $^3A_2$ in FIG. 3, is a deep level state in the band gap. The first excited state, labeled as $^3E$, is 1.94 eV above the ground state. While it is less localized, it is still more than 1 eV from the conduction band. The 1.94 eV difference between the two bound states corresponds to the observed 638 nm zero phonon absorption and emission line shown on FIG. 4.

While both the ground state and the excited state are S=1 spin triplets, going forward we concentrate on the magnetic sublevels of the ground state only. Thus rather than using the cumbersome state notation in FIG. 3, we will often simply refer to $m_s=0$, or $m_s=\pm1$ states, it being understood we are referring to the ground state.

In the absence of applied fields, the degeneracy of the $m_s=0$ and $m_s=\pm1$ sublevels in the ground state is lifted first by a large zero field splitting (2.88 GHz) along the NV center axis, reflecting the strongly non-spherical wave function of the 6 electrons. In the presence of applied magnetic and/or electric fields, the $m_s=+1$ and $m_s=-1$ sublevels are further split. For fields parallel to the NV center axis, the splitting is 2.8 MHz per gauss for a magnetic field, and 3.5 mHz per V/m for an electric field. Note that the figure does not represent energy differences to scale, the magnetic sublevels splitting being about 5 orders of magnitude smaller than the principal split (1.95 eV) between the ground sate and the excited state.

Figure 5:
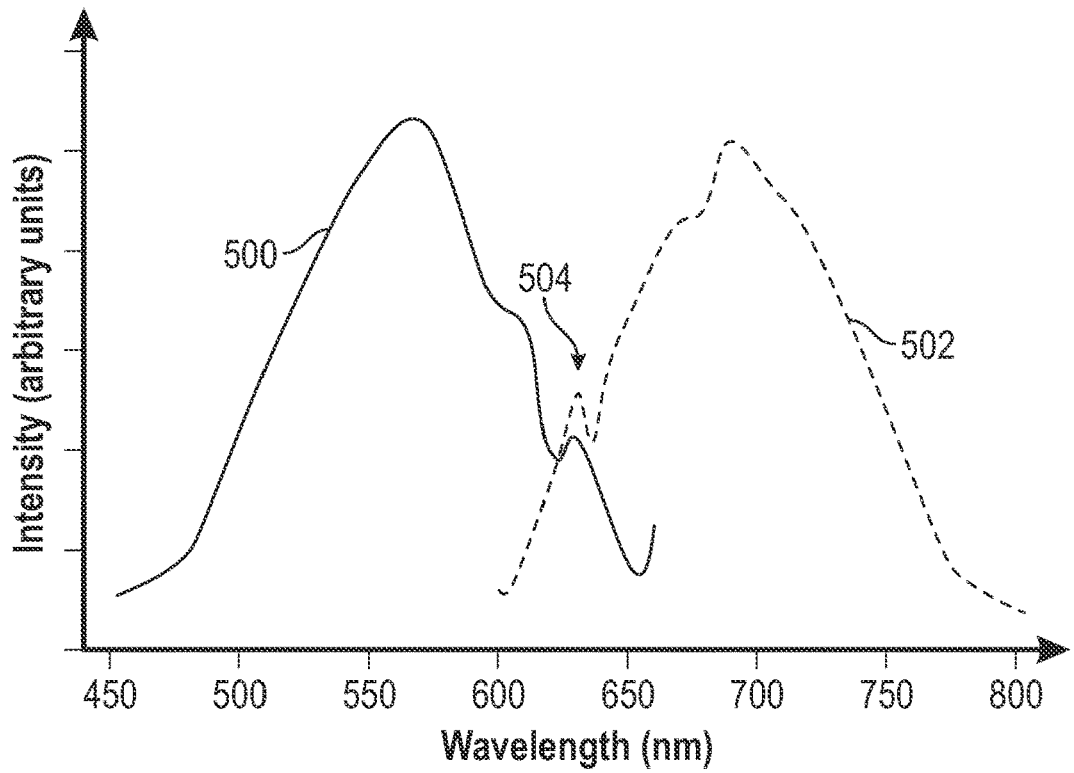
FIG. 5 depicts exemplary optical absorption and emission spectra of an NV center, according to aspects of the present teachings.

Transitions between the ground-state sublevels 400 and 402, and the excited states 406 and 408 lie in the visible range and give rise to the interesting photoluminescent properties of the NV center. FIG. 5 depicts exemplary optical absorption and emission spectra of an NV center at room temperature, according to aspects of the present teachings. The absorption spectrum 500 peaks around 570 nm, and shows how efficiently photons of given wavelengths are absorbed by the NV center. The emission spectrum 502 peaks around 690 nm, and shows the relative intensity of light emitted at given wavelengths. The absorption of photons of any wavelength in the absorption spectrum can lead to emission of photons of any wavelength in the emission spectrum. The spreading of the spectra from the expected discrete wavelengths is due to dissipation of vibrational energy into the molecular lattice, or absorption of thermal energy from the molecular lattice. Both spectra share a peak 504 where the energies of the absorbed and emitted photons are identical. This peak is called the zero phonon line, and is where these spectra would converge to as the ambient temperature approaches absolute zero and lattice vibrations are frozen out.

More specifically, both the absorption and emission spectra show a vast phonon broadening resulting in a strong absorption coefficient, a short (~4 ns) lifetime for the excited state and a practically non-bleaching, intense fluorescence.

The direct absorption and emission paths leave both S and $m_s$ unchanged (the angular momentum of the absorbed or emitted photon is compensated by a "molecular" orbital momentum change). In contrast, the strong phonon coupling also allows for alternative decay path(s) (via inter-system crossings), which change $m_s$ by one, as shown on right side of FIG. 3. This decay path goes through multiple intermediate states, and any photon energy emitted are much further into the infrared compared to photons generated by the direct path. Hence this is often called a "dark path", and is taken with a higher probability for electrons excited from the $m_s=\pm1$ sublevel than those excited from the from the $m_s=0$ sublevel. The net result is a higher visible fluorescence intensity for electrons excited from the $m_s=0$ sublevel of the ground state compared to those excited from the $m_s=\pm1$ sublevels.

Figure 6:
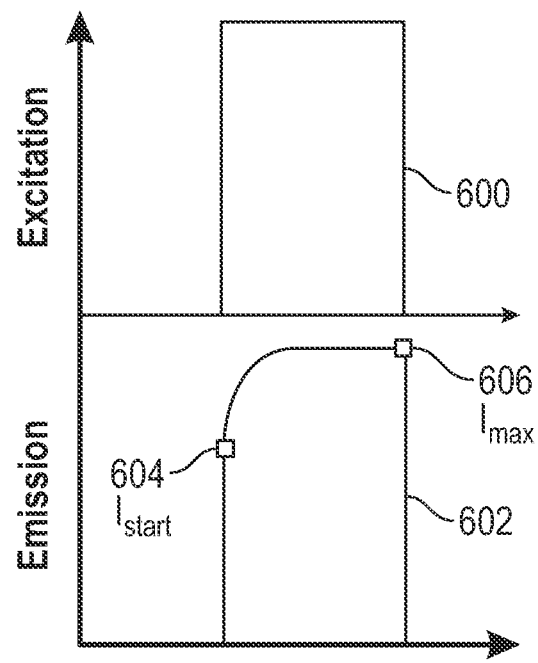
FIG. 6 is a schematic representation of reading and spin polarizing an NV center optically, according to aspects of the present teachings.

FIG. 6 is a schematic representation of reading and spin polarizing an NV center optically, according to aspects of the present teachings. An excitation pulse 600 irradiates a nitrogen-vacancy center, stimulating an emission pulse 602. The initial intensity 604 of the emission pulse, $I_{start}$, is the lowest point of the pulse and is indicative of the relative population of the $m_s=0$ and $m_s=\pm1$ states at the beginning of the measurement. The intensity rises rapidly to the maximum intensity 606, $I_{max}$, as the spin states become polarized to the $m_s=0$ state.

Changes in the magnetic sublevel populations are exactly what are observed via Electron Paramagnetic Resonance, EPR, where the frequencies of the applied microwave excitations match the splittings of the $m_s$ sublevels. The fluorescence intensity depends on the sublevel populations as described above, allowing Optical Detection of the ground states's Magnetic Resonance (ODMR) on NV centers. Note that while we will continue to refer to ODMR detection, direct electrical detection of photocurrents in NV centers have been demonstrated and could serve as an alternative detection mechanism.

Traditional magnetic resonance applies continuous or pulsed microwave/RF electromagnetic fields to induce transitions between or to mix the magnetic sublevels of large ($>10^{13}$) numbers of spins at the same time, i.e. operating on the macroscopic (ensemble average) magnetization, which depends on the temperature. At zero absolute temperature all spins are in their lowest energy sublevel and the system magnetization is maximum, therefore this state is 100% spin polarized. At finite temperature the sublevel population follows Boltzmann statistics, decreasing the ensemble-averaged polarization with increasing temperature. At room temperature—as the energy difference between the sublevels is very small—the population of the different magnetic sublevels is almost equal, resulting in only a 0.1% polarization.

Magnetization originating from the population difference of the sublevels is referred to as the longitudinal magnetization, or the z component of the magnetization as conventionally the z-axis is chosen parallel with the quantization axis. At any temperature, the longitudinal magnetization has an equilibrium value which is proportional to the spin polarization. The transverse magnetization, the XY component of the magnetization, is the ensemble-average of mixed states (as the eigenstates lie along the z direction). Its equilibrium value is zero.

Sublevel transitions or mixed states (with temporarily non-zero ensemble average of the transverse magnetization) can be created by applying RF/microwave electromagnetic fields with photon energies matching the energies of the sublevels splitting E. The corresponding frequency is defined by $E=hf_L$, where h is the Planck constant and $f_L$ is known as the Larmour frequency. The mixed states (and hence the ensemble average transverse magnetization) precess (rotate) at the Larmour frequency. Typically, the EMF induced by this rotating macroscopic magnetization is detected through a coil or resonator.

After the creation of mixed states, the transverse magnetization signal decays in time principally for two reasons:

1. The individual spins experience different fields or changing fields during the precession, i.e. the energy difference of the $m_s$ sublevels are different, therefore the precession frequency of the mixed states are slightly different. While they begin precessing in phase, phase differences will build up due to the differences in the precession frequencies and the ensemble average (vector sum) transverse magnetization will go to zero. As the precessing macroscopic magnetic moment decays to zero, naturally the induced signal decays as well. The characteristic time of this decay, caused by the loss of "phase coherence" is referred to as $T_2$ or the transverse relaxation time. In more elaborate experiments, decay due to static field differences (i.e. magnetic field inhomogeneity over the sample) is eliminated and the decay time, reflecting only dynamical changes during the measurement, is then referred to as phase memory time $T_M$. Loss of the transverse magnetization in this fashion does not require energy exchange with the environment.

2. At finite temperatures, spins can exchange energy with the environment and flip from one sublevel to another, i.e. the eigenstates have a finite lifetime due to interactions with the environment. More precisely, the fluctuating (time dependent) electromagnetic field generated by the environment has to have a non-zero Larmour frequency field component in the transverse direction to induce a state change. As a result of these changes, the precessing transverse magnetization will be lost as the magnetization turns back to the z (or longitudinal) direction. The characteristic time associated with this process (the time required to return to thermal equilibrium population distribution of eigenstates) is called $T_1$, or longitudinal relaxation, or spin-lattice relaxation time, as it requires energy exchange with the environment. This process imposes an upper limit on any precession decay times, such as $T_2$ and $T_M$.

Unlike traditional EPR detection, ODMR detects the longitudinal magnetization. The loss of transverse detection and its advantages, however are abundantly compensated by a huge sensitivity gain: low energy magnetic sublevel transitions can be observed via optical photons with 100,000 times greater energy, at near perfect quantum efficiency.

Besides allowing for ODMR detection, in isolated NV centers the $m_s$ dependent fluorescence also allows manipulation of the sublevel populations. This is because the lifetime of the magnetic sublevels are much longer than the fluorescence lifetime. At high enough excitation intensities, the fluorescence rate is limited only by the fluorescence lifetime and can be 100 MHz or higher. For example, if an excitation from the $m_s=\pm1$ sublevel of the ground state has a w=0.7 probability of retaining its quantum number and a 0.3 probability of returning to the $m_s=0$ sublevel via the dark path, then after 10 cycles the probability to find any of the spins in the $m_s=0$ state will be 98%, i.e. a 98% spin polarization can be built up for a macroscopic sample. As $T_1$ of NV centers is typically much longer than 100 microseconds, a sufficiently intense 100 ns pulse can create a spin polarization equivalent to cooling the diamond from room temperature to 0.3K. Starting any magnetic resonance measurement with a nearly fully spin polarized state is a 1000× gain in signal compared to starting with the room temperature equilibrium spin polarization.

The same pulse that polarizes the spin population also acts as a measurement of the spin polarization, as shown in FIG. 6. The maximum fluorescence arises when the sample is 100% spin polarized in the $m_s=0$ sublevel. We define that maximum fluorescence intensity as $I_{max}$. If we use the probabilities from the above example, assuming we are starting in thermal equilibrium, then when the excitation light is turned on at t=0 the fluorescence response will be 80% of $I_{max}$ corresponding to ⅓ of the population in the $m_s=0$ sublevel fluorescing at max efficiency and ⅔ in the $m_s=\pm1$ states fluorescing at 70% efficiency (⅓+⅔*0.7=0.8). The intensity will asymptotically approach $I_{max}$ at a rate determined by the intensity of the excitation light.

In this case, the initial polarization of the $m_s=0$ sublevel, $P_0$, can be expressed in terms of the initial fluorescence intensity $I_{start}$, as $$P_0 = \frac{1}{(1-w)}\left(\frac{I_{start}}{I_{max}} - w\right)$$

In the case where w=0.7 analyzed above, if $I_{start}=I_{max}$, then $P_0=1$. If $I_{start}=0.7*I_{max}$ then $P_0=0$. If $I_{start}=0.8*I_{max}$, then $P_0=\frac{1}{3}$, etc.

The unique properties of the NV center outlined above means that it is easy to construct an experimental setup which is able to detect the fluorescence of a single NV center using a commercial fluorescence microscope. As the NV centers can be separated by hundreds of nanometers, the fluorescence of single NV centers observed with the microscope carries all the spectroscopic information of the magnetic sublevels of a single spin. As a single spin is being observed there is no ensemble average as is the case in traditional EPR measurements, but there is still a direct correspondence between ensemble average and the time average of the single spin. To relate the two, polarization values of the ensemble average have to be replaced with probabilities of sublevels, i.e. an optical excitation pulse which leads to 98% $m_s=0$ spin polarization of a macroscopic ensemble will translate to finding the single NV center in an $m_s=0$ state with 98% probability. Thanks to the high fluorescence, fast repetition and efficient time averaging, reasonably short experiment times with small statistical errors can be achieved.

The properties of NV centers are well suited for time domain magnetic resonance: the 100% polarized initial state, single center sensitivity detection, and long relaxation times, plus the fact that all time-domain rf/microwave pulse sequences ever invented for sophisticated, high resolution spectroscopy can be applied, render a single NV center one of the most sensitive quantum measurement tools available.

Figure 7A:
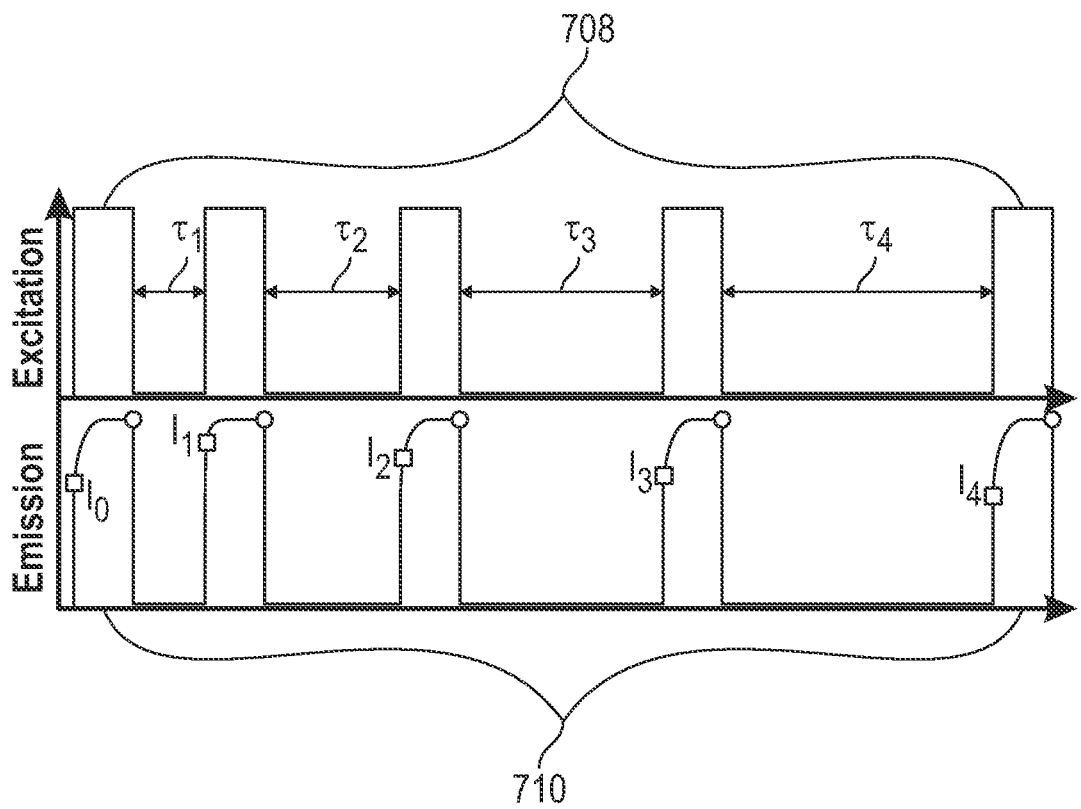
FIG. 7A is a schematic representation of excitation and emission pulses associated with an NV center, according to aspects of the present teachings.
Figure 7B:
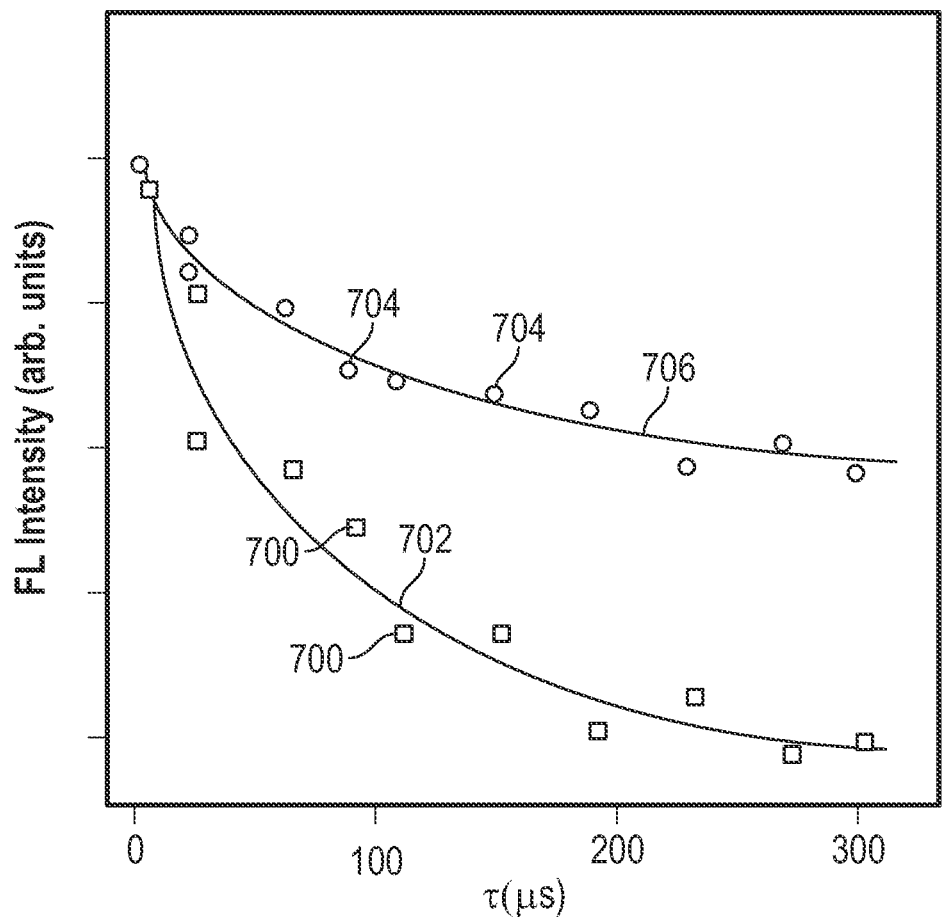
FIG. 7B is a graphical representation of NV center emission intensity, comparing the intensity as a function of time in the absence and presence of a bound target molecule, according to aspects of the present teachings.

FIGS. 7A-7B depict a means to measure the relaxation time, $T_1$, through a purely optical measurement. The $m_s=\pm1$ spin sublevels emit with a fluorescent intensity approximately 70% of that of the $m_s=0$ sublevel, so that if equally partitioned, the total fluorescent intensity is about 80% of what it would be if the spins are fully polarized into the $m_s=0$ sublevel. A series of pulses, as in FIG. 6, allow for measurements to assess the relative populations of the $m_s=0$ and $m_s=\pm1$ sublevel and also repolarize the spins into the $m_s=0$ sublevel.

FIG. 7A is a schematic representation of optical excitation pulses 708 and emission pulses 710 associated with an NV center, according to aspects of the present teachings. An NV center in diamond is irradiated with a series of pulses of excitation light, each of long enough duration to cause full polarization of the NV center into the $m_s=0$ sublevel. The spacing $T_1$ between these excitation pulses is varied. The fluorescent intensity immediately after the start of the excitation pulse (filled squares $I_0$, $I_1$ . . . ) is measured, as is a reference intensity (open rectangles), taken when the spin states should be fully polarized in the $m_s=0$ sublevel.

FIG. 7B is a graphical representation of NV center emission intensity, comparing the intensity as a function of time in the absence and presence of a bound target molecule, according to aspects of the present teachings. More specifically, the difference between the initial intensities and the reference intensities in FIG. 7A is plotted as a function of the time spacing $T_1$ between them and shows how long is required for the sublevels to return to thermal equilibrium. An exponential fit of form Intensity=$I_0$*exp($-\tau/T_1$) yields a direct measure of $T_1$. The data points 700 show a faster return to equilibrium and thus their exponential fit 702 would yield a shorter $T_1$ than the data points 704 and their exponential fit 706. Different $T_1$ values arise as a consequence of an analyte being bound or not bound to the aptamers.

More specifically, in FIGS. 7A-7B, a series of excitation pulses of sufficient duration and intensity to optically polarize the NV center are applied with variable waiting times between them. This excitation wavelength is shorter than the zero phonon line, and in practice 532 nm is often used. At the same time the excitation pulses are applied, the emission from the NV center is monitored in a bandwidth that includes some or all of the emission spectrum 502.

Initially, the ground state is thermally equilibrated, thus the initial level of fluorescence $I_0$ corresponds to a level less than the maximum possible $I_m$ because the $m_s=\pm1$ and $m_s=0$ states are almost equally populated. Over the course of the initial pulse, the emission grows to a maximum and saturates at $I_m$ as the $m_s=0$ state becomes populated due to the dynamic spin polarization process explained above. After a waiting time, a second pulse is applied. If the waiting time is short enough, interactions with the surrounding environment will not have had enough time to equilibrate the populations of the ground states and the $m_s=0$ will still be highly populated and thus the initial emission intensity $I_1$ that is measured will still be close the maximum $I_m$.

Spin polarization will again take place during the remainder of the second pulse and the state will again be polarized to $m_s=0$ and a corresponding intensity of $I_m$. A longer waiting time then ensues, and whole process is repeated again. As this process is repeated eventually the waiting time will become substantially longer than the relaxation time of the NV center, and the ground state will be thermally equilibrated and all three sublevels will be equally populated and the initial emission measured will be equal to $I_0$ again.

By plotting the initial emission intensity $I_1$, $I_2$, $I_3$ . . . as a function of the waiting time, a graph such as that in FIG. 7B can be generated. A fit to the graph can yield the relaxation time $T_1$, of the NV center. FIG. 7B shows an example of two data sets and their respective fits corresponding to different $T_1$ values. Note that this measurement sequence is highly analogous to that used in a standard pulsed magnetic EPR experiment, where the initial state is the inverted thermal equilibrium magnetization $-M_0$, prepared by a microwave $\pi$ pulse and the later time value is read out by detecting microwave radiation initiated by another microwave $\pi/2$ pulse. However, in this case no magnetic field or microwave antenna or resonator is required, thus considerably simplifying the measurement.

With the addition of microwaves, more detailed measurements techniques become possible. For example, in the case of the purely optical $T_1$ measurement explained above, a microwave $\pi$ pulse (with the frequency of the zero-field splitting and with the field oriented perpendicular to the NV center symmetry axis) added right after every polarizing light pulse would provide an initial population of zero for the $m_s=0$ state. By alternating the measurement with and without microwave pulses and plotting and fitting their difference, one could measure $T_1$ without the need of fitting for the value of the residual (thermal equilibrium) signal. Note, that this works so simply because in the absence of an external magnetic field the $m_s=+/-1$ states are degenerate (equal energy).

Adding an external field further increases the possibilities for measurement. When an external static field $H_0$ is imposed, the $m_s=\pm 1$ states energy levels split, so the $m_s=0$ to $m_s=+1$ and the $m_s=0$ to $m_s=-1$ transitions will respond to different frequency microwave excitations. As long as the applied field is small or parallel with the NV center symmetry axis the optical response will not change and can continue to be used for readout. Optical polarization of the $m_s=0$ state continues to serve as an ideal starting point for experiments and the initial fluorescence intensity measured during an optical excitation pulse at a later time can be used to measure the population of the $m_s=0$ sublevel, i.e. serve as sensitive longitudinal detection. The time interval between the initial polarization and the detection can be varied and used to perform sublevel spectroscopy between levels selected by the frequency of the microwave pulses. Note than an external electric field will also split the sublevels and can be used rather than an external magnetic field.

All known microwave pulse sequences ranging from simple Hahn echos, Carr-Purcell-Meiboom-Gill (CPMG), to MREV-8 can be used to explore the NV centers coherence time, i.e. determine small field variations down to a few tenths of milliGauss over millisecond time scales. The prerequisite for these measurements is a long $T_1$, requiring not only NV centers further from the surface (15-20 nm) but also freezing the motion of the aptamers, proteins and ions. i.e. freezing the liquid studied.

Additionally, distance changes between a spin-label attached to the aptamer and the NV center induced by the protein capture can be measured with Double Electron-Electron Resonance (DEER) experiments. Applying a second microwave excitation at a different frequency to reverse the spin on the spin-label while reversing the precession of the NV sublevels, the precession frequency difference due to the spin reversal can be detected with high precision, enabling sub-nanometer precision distance measurements up to 20 nm. To perform DEER over the distances required, the relaxation time of both the NV center and the spin-label on the aptamer will need to be of the order of milliseconds, again requiring freezing the liquid being studied.

As described above, the lateral separation between the NV centers may be large, such as more than 100 nm, to prevent significant interactions between NV centers. The aptamers, however, are small, of order a few nanometers, so we distinguish two different realizations. In the first, aptamers are bound to the surface densely so that any given NV center interacts with multiple aptamer sites distributed randomly within the NV center's range of interaction and thus measures an average interaction change across the multiple sites.

In a second possibility, site-directed surface chemistry is used to ensure a one to one pairing between aptamer sites and underlying NV centers. This can be achieved by using surface chemistry influenced by the charge present in the NV center, or by the fluorescence of the NV center. This configuration has the advantage of producing nearly identical measurement sites affording single protein sensitivity and the ability to discriminate non-specific binders from the correct target proteins. This ability to assemble statistics on the basis of yes or no decisions on a molecule-by-molecule basis means that given the same number of NV centers, the second configuration may provide superior resolution and dynamic range.

One goal of the present teachings is to measure the concentration of multiple proteins simultaneously by using aptamers specific to each individual protein. There are at least two fundamentally different ways that this can be accomplished.

In a first possible detection paradigm, for any given protein target there are a number of individual NV centers and aptamer sites that are each measured by an independent detector. This is effectively running a multitude of single NV center experiments. If there is further a one-to-one pairing between NV centers and aptamer sites, then one can count the number of bound proteins to generate a single number indicative of the concentration for that specific target protein.

In the second possible detection paradigm, a multitude of NV centers and aptamer sites for a given protein target are measured simultaneously by a single detector. While this foregoes the molecule-by-molecule discrimination advantages and will require creating calibration curves to quantify the concentration of the target protein, it may reduce the required complexity of the device.

In either case, ideally all NV centers are excited and detected at the same time, however, that does not preclude using multiple measurement protocols to address the fact that different aptamers may have different responses.

For both cases, different portions of the diamond (or more generally, crystalline) surface will be dedicated to measuring the concentration of different proteins. However, a difference arises in the number of detectors required. For example, detecting the concentration of 10,000 proteins could require on the order of $10^8$ detectors in the first case, but would only require 10,000 detectors in the second case.

FIGS. 8A-8D depict different configurations for probing a biochip based on the present teachings. While identical NV centers lying along the [111] direction close to a (111) terminated diamond surface would be an ideal configuration because all NV centers being measured are equivalent and the most sensitive detection area is located directly above the NV center, other constraints, such as which orientation diamond crystals can be easily manufactured, may not allow this. Some device configurations will be more forgiving of this situation than others.

Figure 8A:
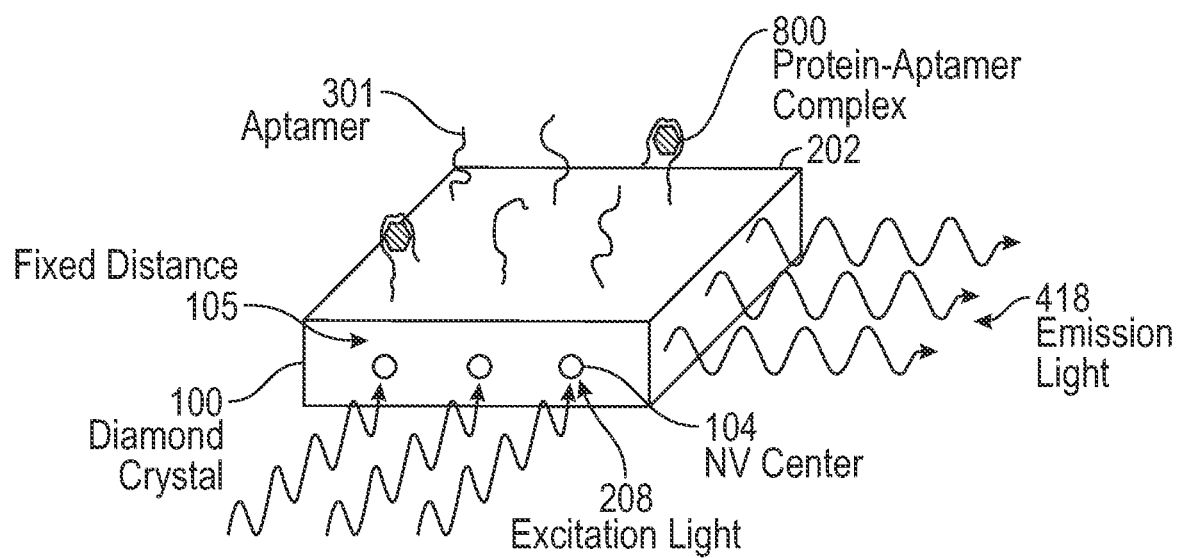
FIG. 8A depicts a first illustrative configuration of a device for detecting target molecules, according to aspects of the present teachings.

FIG. 8A depicts a first illustrative configuration of a device for detecting target molecules, according to aspects of the present teachings. In the simplest configuration aptamers 301 are attached to the surface of a diamond crystal 100, in close proximity to nitrogen-vacancy centers 104 located at a prescribed depth below the sensing surface 202. Properties of the fluorescent emission light 418, which is induced or stimulated by excitation light 208, are measured in order to detect the presence of protein-aptamer complexes 800. The presence of the protein induces a change in one or more properties of the nitrogen-vacancy center, and the change is detected based on the fluorescent emission from the nitrogen-vacancy center.

The configuration shown in FIG. 8A is all that is required to perform the all-optical $T_1$ measurement described above. It imposes the least stringent conditions for the NV center equivalence. A (100) diamond surface with all 8 different possible NV center orientations could be used. In this case the NV center symmetry axes won't be perpendicular to the surface, which isn't ideal, but all 8 orientations will be misaligned by the same amount so the NV centers perform equivalently. One disadvantage is that due to details of the dipole-dipole interaction, magnetic interactions directly above the NV centers are minimized, so the most sensitive interaction area is located some lateral distance away from each NV center. This isn't true for electric interactions. The orientation also isn't ideal for optical excitation and readout using light totally internally reflected inside the diamond. However, it does represent a decent compromise between both and allows use of a diamond surface which is easier to manufacture.

Figure 8B:
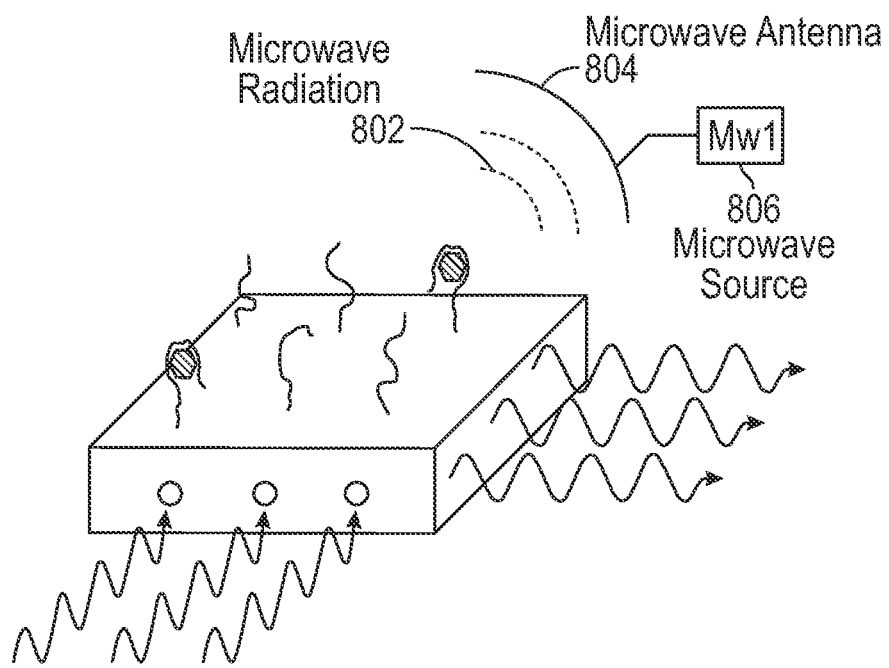
FIG. 8B depicts another illustrative configuration of a device for detecting target molecules, according to aspects of the present teachings.

FIG. 8B depicts another illustrative configuration of a device for detecting target molecules, according to aspects of the present teachings. To the configuration depicted in (A) is added a microwave source 806, from which microwave radiation 802 is directed to the diamond surface by means of a microwave antenna 804. The microwave source matches the zero field splitting frequency (2.89 GHz), and can be added as in FIG. 8B in a direction that assures the angle of the microwave magnetic field is the same relative to all the NV centers as well to help the measurement accuracy. The intensity of fluorescent emission light 418 may be measured, and a resonance behavior of a color center within the diamond may be identified based on a relationship between the measured intensity and the frequency of microwave radiation 802.

Figure 8C:
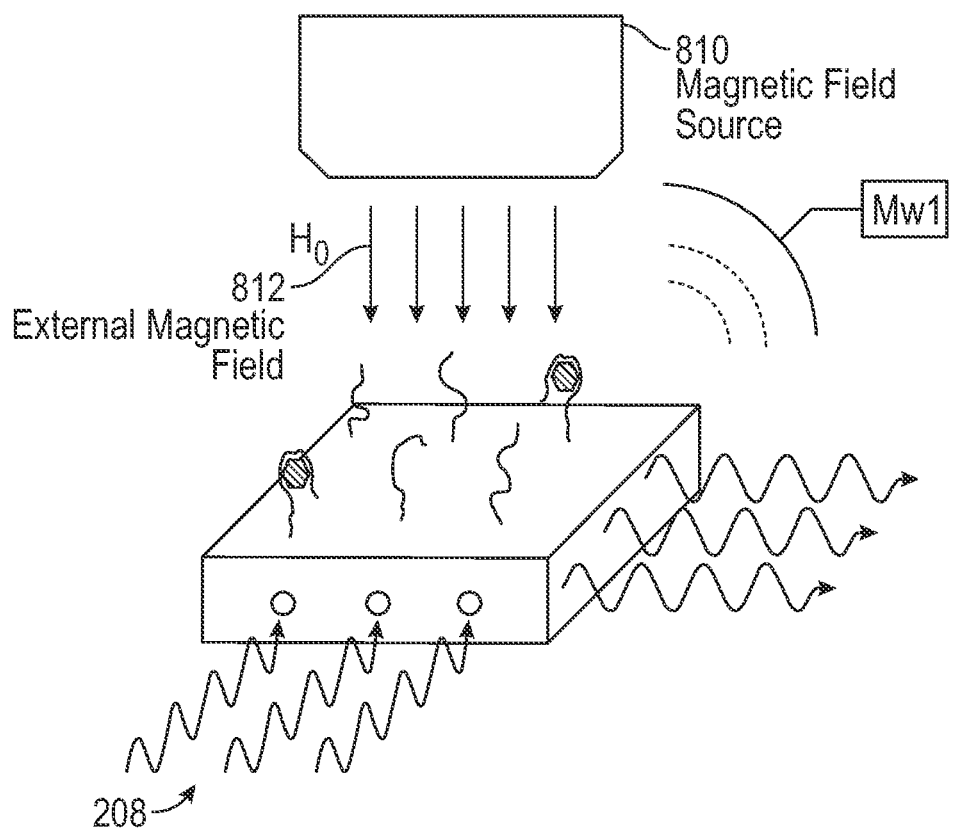
FIG. 8C depicts yet another illustrative configuration of a device for detecting target molecules, according to aspects of the present teachings.

FIG. 8C depicts yet another illustrative configuration of a device for detecting target molecules, according to aspects of the present teachings. To the configuration depicted in (B) is added a magnetic field source 810, by which an external magnetic field 812 is imposed on the diamond surface. Adding an external static field $H_0$ as indicated on FIG. 8C may be required for phase coherence ($T_2$) measurements.

Figure 8D:
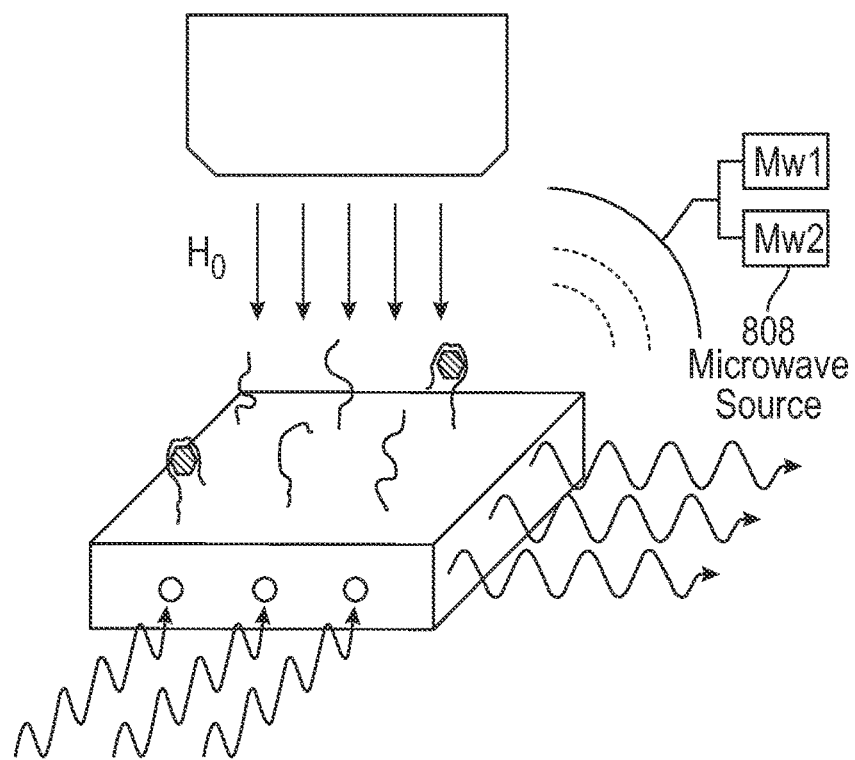
FIG. 8D depicts still another illustrative configuration of a device for detecting target molecules, according to aspects of the present teachings.

FIG. 8D depicts still another illustrative configuration of a device for detecting target molecules, according to aspects of the present teachings. To the configuration depicted in (C) is added a second microwave source 808 which shares the same microwave antenna 804 as the first microwave source 806. A second (independent frequency) microwave source as shown in FIG. 8D may be required for the spin-labels to perform DEER experiments—note that all microwave magnetic fields are ideally close to perpendicular to $H_0$. Because at high magnetic fields, only NV centers parallel with the field can be read out optically, this configuration would ideally use a (111) surface with NV centers aligned along the [111] direction as described above. If all NV center orientations were populated equally, 75% of them would be unusable. Optical excitation and fluorescence emission are ideally close to parallel with the NV axes.

In the case of non-equivalent NV centers (like the (100) terminated crystals with all 8 different orientations populated) a possible solution is to use only ⅛ of the NV centers with the field properly aligned relative to them, or to address them all sequentially by applying different field orientations and microwave frequencies. Another possible solution is to use what is known as "field cycling" in the magnetic resonance field. In this case, a large field (e.g., bigger than two times the zero field splitting) could be applied along the [100] axis during the microwave operations and switched to zero during optical polarization and detection operations.

Figure 9:
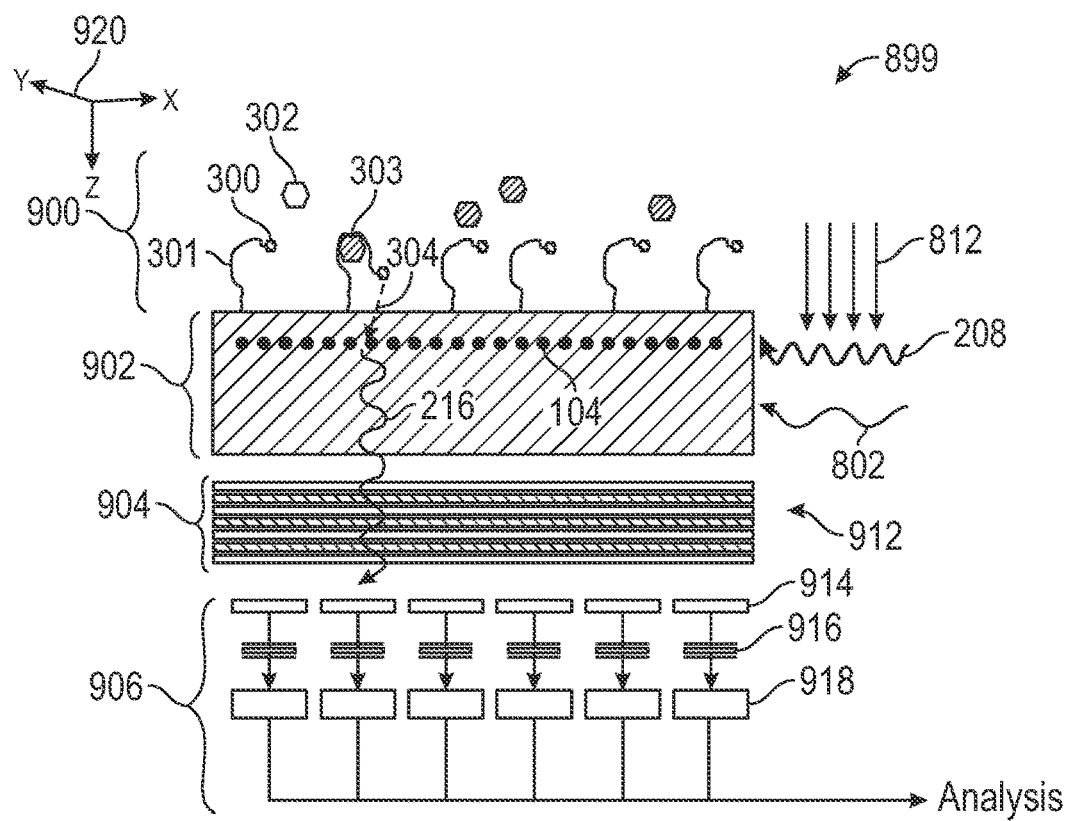
FIG. 9 depicts still another illustrative configuration of a device for detecting target molecules, according to aspects of the present teachings.

FIG. 9 depicts still another illustrative configuration of a device 899 for detecting target molecules, according to aspects of the present teachings. More specifically, FIG. 9 is a schematic representation an integrated biochip based on the invention (not to scale). Although this figure depicts an embodiment of the detection technique that utilizes spin labels, aptamers, and nitrogen vacancy centers, other embodiments of the detection technique are possible. The biochip is comprised of four layers: the Capture Layer 900, the Diamond layer 902, the Filter Layer 904, and the Integrated Detection and Processing Layer 906. The Capture Layer 900 is comprised of a channel that directs the sample fluid containing the target molecule 206 of interest (e.g., target protein 302) past the surface of the Diamond Layer, on which are attached SOMAmers 301, linked to magnetic spin labels 300.

Features in the Capture Layer are regions of the sensing surface of the Diamond Layer on which identical SOMAmers are attached. Each feature contains one or more SOMAmers specific to a separate protein analyte, and corresponds in x-y coordinates (FIG. 9) to an associated collection of NV centers in the Diamond Layer and to an individual photodetector in the Integrated Detection and Processing Layer.

Each SOMAmer 301 or other capture reagent 200 may be a specific type or species of capture reagent configured to bind to a specific type or species of target molecule 206. The species of the capture reagent may be associated with a functional group of the capture reagent. Capture layer 900 may include capture reagents 200 belonging to at least two different species, such that at least two species of target molecule 206 may be detected by the biochip device. In some embodiments, Capture layer 900 includes capture reagents from a large number of species, e.g., hundreds of species, thousands of species, or more.

Some preferred embodiments of the present invention do not include spin labels. Binding of a protein molecule to a SOMAmer molecule results in a change in the interaction 304 between the SOMAmer and proximal nitrogen-vacancy centers 104, such changes being detected via fluorescent emission 216. The surface chemistry and SOMAmer are optimized to create a large relative difference in interaction upon binding of a protein target to the aptamer.

The Diamond Layer is comprised of high purity diamond fabricated by chemical vapor deposition, in which a layer of NV centers 104 is embedded at a prescribed fixed distance 105 from the surface. In some examples, the prescribed fixed distance, which may also be referred to as a depth, is in a range of 5-20 nanometers, or 15-20 nanometers. The NV centers within the Diamond Layer are separated by a distance much greater than the prescribed fixed depth, assuring the interactions between them are small compared to interactions with molecules on the surface. The thickness of the layer of NV centers is small compared to the prescribed fixed depth. The distance between the nitrogen-vacancy centers and the SOMAmers is chosen to be sufficiently small that the change in interaction upon binding the protein to the SOMAmer is possible and/or detectable. An external magnetic field 812 may be present. The Diamond Layer may include 100% $^{12}C$ diamond.

Excitation light 208 (produced by an optical source such as a laser) stimulates fluorescence of the NV centers. External microwaves 802 transition ground-state electrons between their sublevels. The Filter Layer is comprised of layered dielectric materials to form a dichroic bandpass filter 912, which is adhered to the Diamond Layer 902 on one side, and the Integrated Detection and Processing Layer 906 on the other side. In addition to passing emitted light from the NV centers while blocking all other wavelengths, the Filter Layer 904 also blocks emitted light that is outside a narrow range of angles from normal, thereby minimizing crosstalk in detection between neighboring NV centers.

The Filter Layer is designed to be a narrow band-pass filter around the emission wavelength of the nitrogen-vacancy centers (689 nm). In addition, the Filter Layer blocks light outside of a narrow band of angles from the normal, in order to minimize cross talk between neighboring features. The Filter Layer also serves as a mechanical linkage between the Diamond Layer and the Integrated Detection and Processing Layer. Optically clear and mechanically rigid adhesive may be used to join the Filter Layer to the Diamond Layer at the top, and to join the Filter Layer to the Integrated Detection and Processing Layer at the bottom. The Filter Layer is constructed of layers of dielectric materials that rely on wave interference principles to block certain wavelengths of light. The design and fabrication of the Filter Layer falls outside the purview of the present teachings.

The Integrated Detection and Processing Layer 906 is comprised of CMOS avalanche photodetectors 914 which drive high-speed electronic gates 916 which drive electronic event counters 918. Photodetectors 914 may also be referred to as a detector assembly. According to the present teachings, a detector assembly may be configured to irradiate color centers with excitation light of one or more frequencies, and to detect emission of electromagnetic radiation from the color centers. The output of the event counters is collected for analysis. The designated coordinates 920 are chosen such that the x and y coordinates lie in the plane of the upper Diamond Layer surface, and the z coordinate is perpendicular to the surface. The range of wavelengths emitted by the optical source (i.e., the spectrum of excitation light 208) may or may not be the same as the range of wavelengths detected by photodetectors 914. The range of wavelengths of the excitation light may be partially overlapping or substantially non-overlapping with the range of wavelengths photodetectors 914 are configured to detect.

The Integrated Detection and Processing Layer may be designed for lithographic production, including both the electronic components and connections between them. The Integrated Detection and Processing Layer may be fabricated using lithography and attached to the Filter Layer (or to the Diamond Layer, if the Filter Layer is omitted) using optically transparent adhesive. The Integrated Detection and Processing Layer may be comprised of a photodetector layer, a gating layer, an A to D (analog to digital) layer, and a bus to move accumulated data to a processor. Although FIG. 9 depicts these layers as being distributed in the z-direction, such an arrangement is not necessary.

The photodetector layer may include an array of avalanche photodiodes, each photodiode dedicated to a single feature on the Capture Layer, and being associated with this feature in the x and y coordinates. Each photodiode may be associated with a high-speed electronic gate in the gating layer. Changes in fluorescence from the NV centers can be on the sub-microsecond scale, and so to monitor these changes in intensity it is necessary to collect light only for very short and defined time frames. Each gate in turn is associated with an event counter in the event-counter layer, which actually performs the photon counting. The data from each event counter is bussed to a processor for data analysis.

There are at least three examples of arrangements in which the features of the Capture Layer of FIG. 9 (i.e., regions of the sensing surface of the Diamond Layer on which SOMAmers are attached) could be constructed, each offering different advantages. In a first example, a single SOMAmer is associated with a single NV center, which is in turn associated with a single photodetector. Such a setup offers advantages in terms of detection, but requires precise control of the placement of the NV center or of single SOMAmers. The primary advantage of this mode of construction is that it offers detection of molecules on an individual basis, which allows a third dimension of specificity (after binding affinity and washing) based on binding characteristics which would be lost in ensemble detection. Additionally, target molecules can be counted one-by-one eliminating some calibration steps. The primary disadvantage of this mode is that many such features are required in order to discriminate between different concentrations. Resolving orders of magnitude of differences in concentration may require hundreds or thousands of such features for a single analyte (depending on the desired level of resolution), increasing the complexity of the device.

The second illustrative mode of construction comprises a collection of multiple SOMAmers of the same type associated with a collection of multiple NV centers, which is in turn associated with a single photodetector. The random distribution of NV centers in the x-y plane (as defined in FIG. 9), and the random distribution of SOMAmers in the feature collection, lead to an averaged signal at the photodetector, which should be more stable. A range of concentrations could also be quantified with a single photodetector, due to the multiple SOMAmers. However, using such collections instead of single SOMAmers or NV centers prohibits the third dimension of specificity allowed by the first mode and requires generation of calibration curves to correlate NV center response to the concentration of the target protein in the fluid.

The third mode of construction is a hybrid of the first and second mode, comprising a collection of multiple SOMAmers of the same type being associated with a single NV center, which is in turn associated with a single photodetector. As with the second mode, a range of concentrations could be quantified with a single photodetector, due to the multiple SOMAmers, which also lead to an averaged signal. The use of a single NV center may lead to a cleaner signal. Randomly distributed NV centers may be optically located in the x-y plane, followed by placement of SOMAmer collections at the same location.

Figure 10:
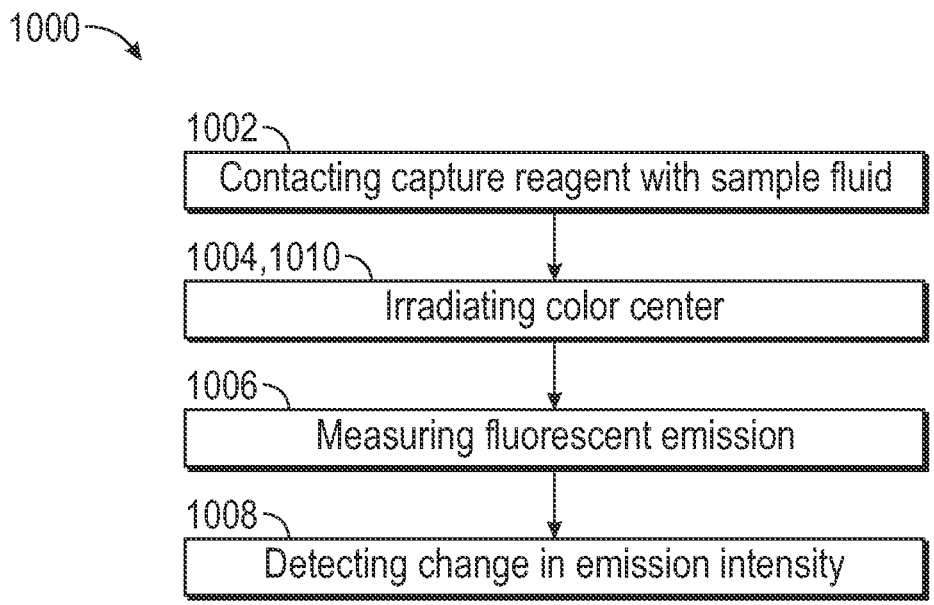
FIG. 10 is a flow chart depicting illustrative steps in a method of detecting target molecules, according to aspects of the present teachings.

FIG. 10 depicts steps performed in an illustrative method 1000 for detecting target molecules in a sample fluid, and may not recite the complete process or all steps of the method. Although various steps of method 1000 are described below and depicted in FIG. 10, the steps need not necessarily all be performed, and in some cases may be performed simultaneously, or in a different order than the order shown.

At step 1002, the method includes contacting a capture reagent with a sample fluid. The capture reagent is attached to a surface (e.g., a surface of a crystalline film or substrate, or a single-crystal diamond) and is configured to bind to a desired target molecule. The capture reagent may be described as captured by the surface, bound to the surface, attached to the surface, tethered to the surface and/or immobilized on the surface. The target molecule may be any target molecule having the ability to bind with a capture reagent, including but not limited to target molecules described in this disclosure, such as a protein. Similarly, the capture reagents may be any suitable capture agents. This includes but is not limited to any of the capture reagents described in this disclosure, such as aptamers, nucleic acid molecules, or nucleic acid molecules having at least one 5-position modified pyrimidine (such as SOMAmers). In some examples, at least two different 5-position modified pyrimidines are attached to the surface, including at least one 5-position modified uridine and at least one 5-position modified cytidine.

At step 1004, the method includes irradiating a color center disposed proximate the surface (e.g., at a fixed depth within the crystalline film) with excitation light. The excitation light is configured (e.g., through selection of central wavelength or bandwidth) to induce fluorescent emission by the color center. In some examples, the color center is a nitrogen-vacancy center of a diamond crystal, and the surface is a surface of the diamond crystal.

At step 1006, the method includes measuring the intensity of the fluorescent emission using one or more detectors (e.g., the photodetectors of the Integrated Detection and Processing Layer described above with reference to FIG. 9).

At step 1008, the method includes detecting a change in the intensity of the fluorescent emission. The intensity changes in response to binding a target molecule to a capture reagent, and therefore changes in the emitted intensity indicate the presence of a target molecule.

Optionally, at step 1010, the method may include irradiating the color center with microwave radiation at a frequency capable of inducing conversion of ground-state electrons in the color center from a first sub-state to a second sub-state. For example, the microwave radiation may include a resonant frequency corresponding to an energy difference between a zero-spin sub-state of the ground state and a non-zero-spin sub-state of the ground state. Detecting a change in the intensity of the fluorescent emission in response to binding of the target molecule at step 1008 may further include identifying resonance behavior of the color center based on a relationship between the measured intensity of the fluorescent emission and the frequency of the microwave radiation. For example, the binding of the target molecule may induce a change in the resonant frequency between the first and second sub-states. The change in the resonant frequency may be identified based on the fluorescent emission intensity measured while varying the frequency of the microwave radiation.

Figure 11:
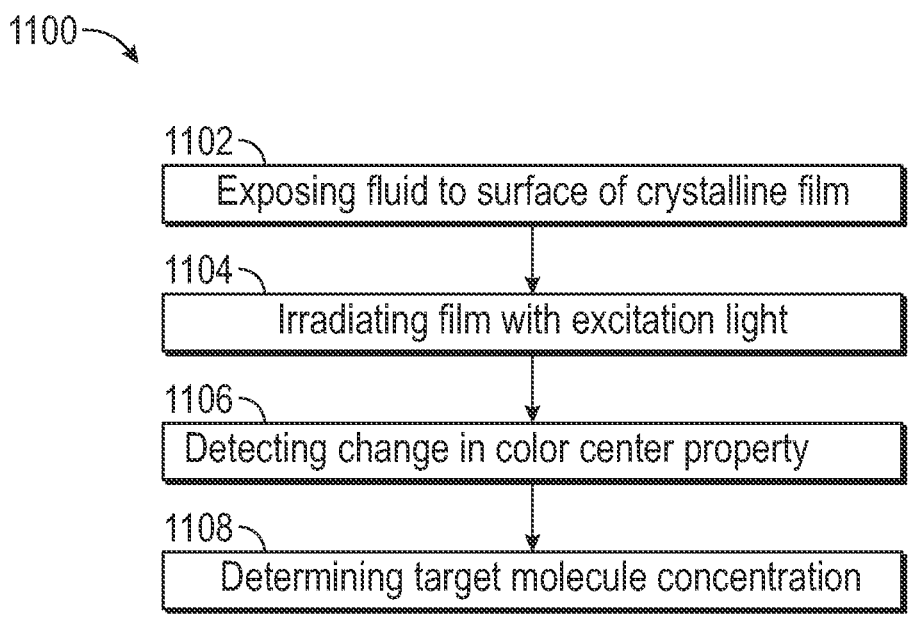
FIG. 11 is a flow chart depicting illustrative steps in another method of detecting target molecules, according to aspects of the present teachings.

FIG. 11 depicts steps performed in an illustrative method 1100 for measuring a concentration of target molecules, and may not recite the complete process or all steps of the method. Although various steps of method 1100 are described below and depicted in FIG. 11, the steps need not necessarily all be performed, and in some cases may be performed simultaneously, or in a different order than the order shown.

At step 1102, the method includes exposing a fluid to the surface of a crystalline film (e.g., a diamond film, among others) to allow capture reagents attached to the surface to bind to target molecules (e.g., proteins, among others) within the fluid. The crystalline film includes at least one color center, such as a nitrogen-vacancy center or other suitable defect.

At step 1104, the method includes irradiating the crystalline film with excitation light configured to induce fluorescent emission from at least one color center within the film. Optionally, step 1104 includes irradiating the color center with microwave radiation having a frequency capable of inducing conversion of ground-state electrons in the color center from a first sub-state to a second sub-state.

At step 1106, the method includes detecting a change in a property of the color center based on the fluorescent emission. The change in the color center property arises in response to binding of the target molecule by the capture reagent. In some examples, the capture reagents include a magnetic spin label, such that binding between the target molecule and the capture reagent changes a magnetic field at the color center. The change in the color center property may be at least partially caused by the change in the magnetic field.

At step 1108, the method includes determining a concentration of target molecules within the fluid based on the detected change in the color center property. For example, characteristics of the detected change may indicate the number or approximate number of target molecules bound by the capture reagents to the surface of the film, and the concentration of target molecules within the fluid can be deduced from the number of target molecules and the volume of the fluid.

Figure 12:
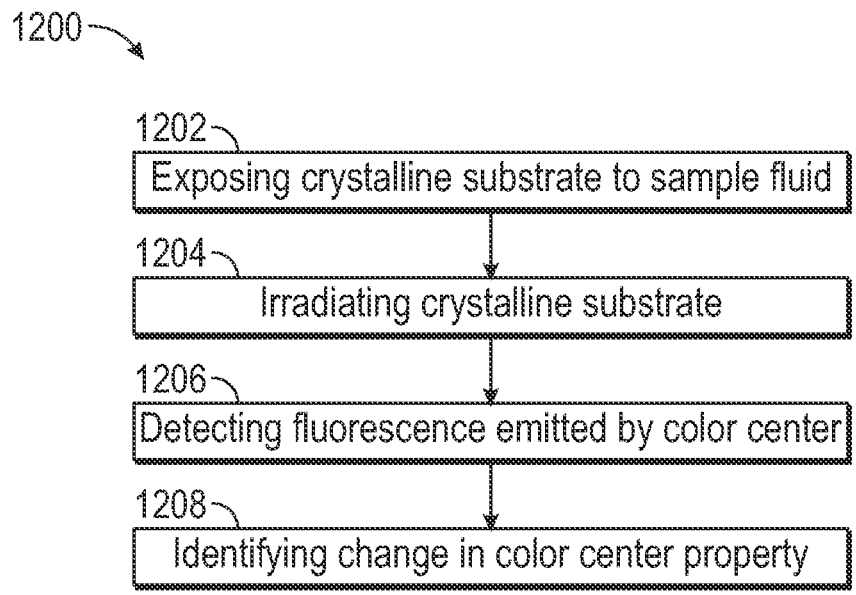
FIG. 12 is a flow chart depicting illustrative steps in yet another method of detecting target molecules, according to aspects of the present teachings.

FIG. 12 depicts steps performed in an illustrative method 1200 for detecting target molecules, and may not recite the complete process or all steps of the method. Although various steps of method 1200 are described below and depicted in FIG. 12, the steps need not necessarily all be performed, and in some cases may be performed simultaneously, or in a different order than the order shown.

At step 1202, the method includes exposing a crystalline substrate (e.g., a diamond film) to a sample fluid, such that capture reagents attached to the surface of the substrate can bind to target molecules expected to be present in the sample fluid. The crystalline substrate includes at least one color center, such as a nitrogen-vacancy center in diamond. The target molecules may be proteins or any other target molecule described elsewhere in this disclosure. Likewise, the capture reagents may be any molecules suitable for binding specifically to the desired target molecules, and may include aptamers, SOMAmers, or the like. In some examples, the capture reagents are aptamers including at least two distinct 5-position modified pyrimidines.

At step 1204, the method includes irradiating the crystalline substrate with electromagnetic radiation. The electromagnetic radiation is configured to stimulate or induce fluorescence by color centers within the crystalline substrate. Characteristics of the electromagnetic radiation, including central frequency, bandwidth, intensity, pulse energy, pulse duration, and/or polarization may be designed to at least partially determine characteristics of the emitted fluorescence.

At step 1206, the method includes detecting fluorescence emitted by the color center, e.g., by one or more photodetectors.

At step 1208, the method includes identifying a change in a property of the one or more color centers caused by binding one or more target molecules from the sample fluid to the capture reagents. For example, identifying the change may include identifying a change in the spectrum of radiation emitted by the color centers, such as detecting fluorescent radiation emitted by the color centers, and may include identifying changes in an intensity, temporal variation, or spectrum of the emitted fluorescence.

Figure 13:
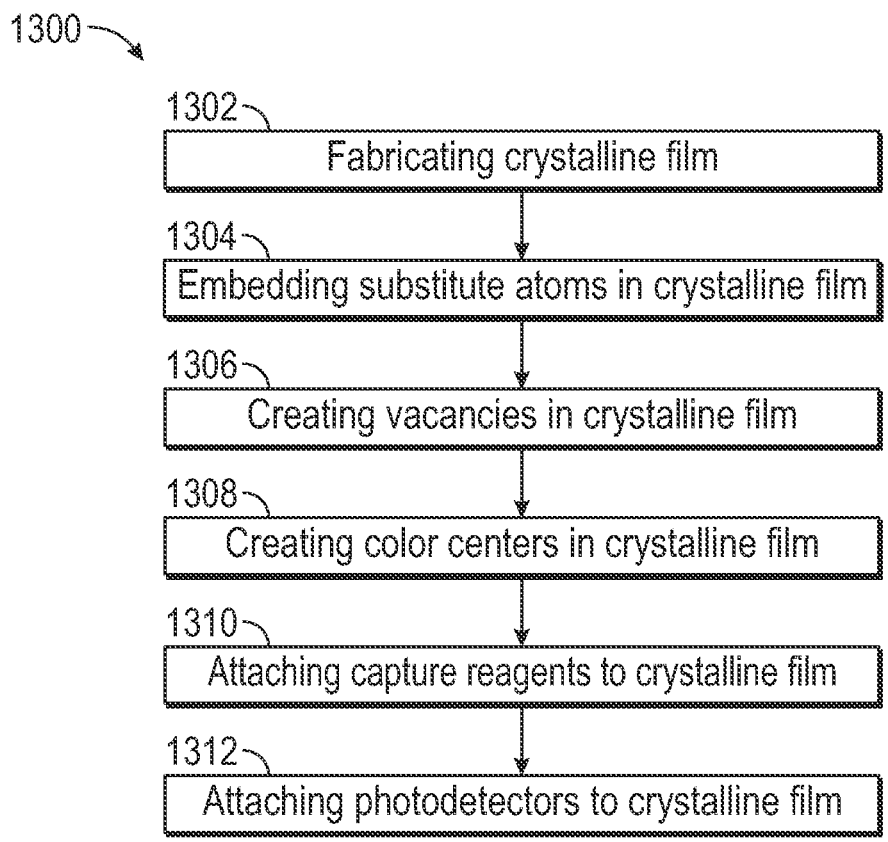
FIG. 13 is a flow chart depicting illustrative steps in a method of manufacturing a device for detecting target molecules, according to aspects of the present teachings.

FIG. 13 depicts steps in an illustrative method 1300 for manufacturing a device for detecting the presence of protein molecules in a sample fluid, and may not recite the complete process or all steps of the method. Although various steps of method 1300 are described below and depicted in FIG. 13, the steps need not necessarily all be performed, and in some cases may be performed simultaneously or in a different order than the order shown. Aspects of method 1300 may, for example, be used to manufacture the integrated biochip depicted in FIG. 9.

At step 1302, the method includes fabricating a crystalline film, e.g., by chemical vapor deposition. For example, $^{12}$C-enriched diamond films may be produced by plasma-enhanced chemical vapor deposition of a mixture of methane and hydrogen gas on diamond substrates.

At step 1304, the method includes embedding substitute atoms in the crystalline film. The substitute atoms are suitable for collocating with vacancies in the crystalline film to form color centers.

At step 1306, the vacancies are created in the crystalline film, e.g., by impinging an ion beam and/or electron beam on the film.

At step 1308, the method includes creating color centers in the crystalline film by collocating at least some of the substitute atoms with at least some of the vacancies. Collocating the substitute atoms and the vacancies may include, for example, annealing the film at a high temperature, or by any other suitable process.

At step 1310, the method includes attaching capture reagents to a first surface of the crystalline film. Step 1310 may include attaching capture reagents to some regions of the surface of the crystalline film, and passivating regions of the surface not bound with capture reagents against non-specific binding by undesired proteins. Attaching the capture reagents and passivating other regions of the surface may be accomplished by binding passivating molecules (e.g., hydrophilic polymers) to the surface, with some of the passivating molecules including active groups for linkage to specific target molecules. For example, some of the passivating molecules may have a first end configured to bind to the surface, and a second end having an active group configured to bind to DNA or other target molecules.

At step 1312, the method includes attaching photodetectors to a second surface of the crystalline film, such that the photodetectors are capable of detecting emission from the color centers. The photodetectors may be fabricated using lithography, and may be adhered to the crystalline film using optically transparent, mechanically rigid adhesive. In some examples, a filter layer (e.g., Filter Layer 904) is included between the photodetectors and the film.

Typical detection schemes for measuring target molecule concentration in a sample fluid include measuring an intensity of fluorescent emission by at least one color center, identifying a change in the fluorescent emission in response to binding of at least one target molecule to a capture reagent, and determining a concentration of target molecules within a sample fluid based on the identified change. For example, aspects of the nitrogen-vacancy center excitation and emission depicted in FIG. 7 may be included in an illustrative method where the relaxation time, $T_1$, is monitored by purely optical methods. $T_1$ is measured by polarizing the ground spin states to the $m_s=0$ sublevel by irradiating the NV centers with excitation light. As shown in FIG. 4, a fraction of the electrons excited from the $m_s=\pm1$ sublevels return to the ground state via the dark transition, thereby undergoing a transition to the $m_s=0$ sublevel, which provides maximum intensity. $T_1$ is determined by periodically monitoring the fluorescent intensity after polarization via excitation has been discontinued and seeing how fast the ground state returns to a fully unpolarized state. An illustrative method for measuring protein in urine includes the following steps, which may be performed simultaneously or in a different order than the order shown:

1. Prepare multiple calibration samples of urine containing known concentrations of the protein of interest,
2. Flow these calibration samples across the sensing surface of the diamond layer, allowing the protein sufficient opportunity to bind to the attached SOMAmers, optionally recirculating the sample fluid,
3. Flow wash fluid across the fluid-contacting surface of the diamond layer, allowing the wash fluid sufficient opportunity to remove molecules binding in non-specific fashion to the SOMAmers, optionally recirculating the wash fluid,
4. Irradiate the NV centers with a series of pulses of excitation light, each pulse of long enough duration to cause full polarization of the NV center into the $m_s=0$ state. The time spacing $T_1$ between these excitation pulses is varied,
5. Measure the fluorescent intensity immediately after the start of each excitation pulse, as well as a reference intensity, taken towards the end of each excitation pulse when the spin states should be fully polarized to the $m_s=0$ sublevel,
6. Calculate normalized intensities by dividing the fluorescent intensity at the start of each excitation pulse with the corresponding reference intensity,
7. Generate response plots for each of the calibration samples, by plotting the reference intensities for each pulse $p_i$ against the spacing time $T_1$ immediately preceding pulse $p_i$,
8. Find the relaxation time $T_1$ for each calibration sample by fitting a decaying exponential of the form normalized intensity=$I_0*\exp(-\tau/T_1)$.
9. Generate a calibration curve of protein concentration versus $T_1$,
10. Repeat steps (2) through (8), using samples of interest instead of calibration samples to generate response plots, and
11. Apply the calibration curve of step 9 to determine the protein concentration of each sample of interest.

Additional methods may involve, for example, systems shown in FIG. 8. While optical detection of the spin state is preferred, the addition of microwave excitation and the introduction of a static field open up all the techniques from traditional EPR for manipulating spin states. Examples of those (e.g., Hahn echoes, DEER, etc.) have been described above. There are a huge number of variations on the method above which add additional spin manipulation steps via techniques well known in the art that can be chosen to optimize detection of the bound analytes.

While the examples given have focused mainly on urine or blood (serum or plasma) as sample fluids, biochips according to the present teachings could work on a variety of biological fluids or solutions derived from them, for example, by dilution. These include blood, plasma, serum, urine, semen, saliva, meningeal fluid, amniotic fluid, glandular fluid, lymph fluid, nipple aspirate, bronchial aspirate, synovial fluid, joint aspirate, leukocytes, peripheral blood mononuclear cells, sputum, breath, cells, a cellular extract, stool, tissue, a tissue extract, a tissue biopsy, and cerebrospinal fluid.

Illustrative Combinations and Additional Examples

This section describes additional aspects and features of proteomic assays, presented without limitation as a series of paragraphs, some of all of which may be alphanumerically designated for clarity and efficiency. Each of these paragraphs can be combined with one or more other paragraphs, and/or with disclosure from elsewhere in this application, including any material incorporated by reference, in any suitable manner.

Some of the paragraphs below expressly refer to and further limit other paragraphs, providing without limitation examples of some of the suitable combinations.

A. A device for detection of one or more species of target molecules in a fluid comprising:
  a) A solid support with a surface; and
  b) One or more species of capture reagents attached to the surface;
  c) Wherein each species of capture reagent binds selectively to a particular species of target molecule; and
  d) Color centers located close to the surface of the solid support; and
  e) A detector or detectors for detecting changes in the properties of the color centers upon binding of protein molecules to the capture reagents.

A1. The device of paragraph A, wherein the fluid contains biological fluids and the target molecules are proteins.

A2. The device of paragraph A1, wherein the capture reagents are aptamers.

A3. The device of paragraph A2, wherein the aptamers are nucleic acid molecules.

A4. The device of paragraph A3, wherein at least some of the nucleic acid molecules have at least one 5-position modified pyrimidine.

A5. The device of paragraph A4, wherein the solid support is a diamond crystal and the color centers are nitrogen-vacancy centers.

A6. The device of paragraph A5, wherein the detector or detectors is an optical system that irradiates the nitrogen-vacancy centers with a first range of wavelengths of radiation and detects a second range of wavelengths.

A7. The device of paragraph A6, wherein the optical source is a pulsed optical source.

A8. The device of paragraph A7, wherein the changes in properties of the nitrogen vacancy centers are changes in the magnetic resonance properties of the nitrogen vacancy centers.

A9. The device of paragraph A8, further comprising a magnetic field source to provide a magnetic field.

A10. The device of paragraph A9, further comprising a microwave source to provide microwave radiation.

A11. The device of paragraph A10, wherein the microwave source is tuned to a frequency resonant with the sublevels of the nitrogen vacancy center electronic ground state.

A12. The device of paragraph A11, wherein the microwave source is a pulsed source.

A13. The device of paragraph A5, wherein the surface of the solid support is a {111} surface of a single crystal diamond.

A14. The device of paragraph A5, wherein the surface of the solid support is a {100} surface of a single crystal diamond.

A15. The device of paragraph A5, wherein the nitrogen vacancy centers are located within 25 nanometers of surface of the diamond crystal.

A16. The device of paragraph A7, wherein the nucleic acid molecules additionally include a spin label.

A17. The device of paragraph A12, wherein the nucleic acid molecules additionally include a spin label.

B. A device for simultaneously quantifying single or multiple analytes in a sample fluid comprising:
  a) A thin crystalline layer, one surface which makes contact with the sample fluid, containing color center defects 5-25 nanometers from the fluid-contacting surface;
  b) Capture agents that are attached to the fluid-contacting surface of the crystalline layer in close proximity to the color center defects described in (a), such that binding of analytes to the binding agents affect the local magnetic field external to the color center defects thus detectably changing the behavior of said color center defects; and
  c) A means of detecting the said change in behavior of said color center defects.

B1. The device of paragraph B, in which the said change in behavior of said color center defects includes a change in fluorescence and the said means of detecting this change in fluorescence comprises:
  a) An optical filter layer bonded to the non-contacting surface of the crystalline layer, for passing fluorescent emissions from the color center defects while excluding excitation light or other light;
  b) A detection layer, bonded to the optical filter layer on the side opposite of the crystalline layer, for the capture and quantitation of the fluorescent light emitted by the color center defects, including the intensity; and
  c) A means for introducing excitation light into the crystalline layer, such that the color center defects are stimulated to emit fluorescent light;

B2. The device of paragraph B1, in which the said means for introducing excitation light into the crystalline layer does such introduction of light through the edges of the said crystalline layer, such that the said excitation light travels in a direction parallel to the said fluid-contacting surface of the crystalline layer.

B3. The device of paragraph B, in which the said change in behavior of said color center defects includes a change in fluorescence and the said means of detecting this change in fluorescence comprises:
  a) An optical wave guide, optionally including an optical filter, bonded to the non-contacting surface of the crystalline layer, for passing fluorescent emissions from the color center defects while excluding excitation light or other light;
  b) A detection layer, situated at the opposing end of the optical wave guide from the said crystalline layer, for the capture and quantitation of the fluorescent light emitted by the color center defects, including the intensity; and
  c) A means for introducing excitation light into the crystalline layer, such that the color center defects are stimulated to emit fluorescent light.

B4. The device of paragraph B, in which the said change in behavior of said color center defects includes a change in the electric field or magnetic field local to the said color center defect and the said means of detecting this said change in electric field or magnetic field comprises an electronic or opto-electronic detector.

B5. The device of paragraph B1, further comprising a means for introducing microwave radiation into the crystalline layer, in order to affect and/or monitor the resonance behavior of the color center defects.

B6. The device of paragraph B5, in which is included a means for imposing a constant or variable magnetic field across the regions containing color center defects in order to modify their resonance behavior.

B7. The device of paragraph B5, wherein the said thin crystalline layer is a diamond film, and the said color center defects are nitrogen-vacancy centers.

B8. The device of paragraph B7, wherein the said device may be regenerated for multiple uses.

B9. The device of paragraph B8, wherein the said analyte-specific binding agents are linked to magnetic spin labels to increase the effect upon binding of said analytes on the local magnetic field external to the color center defects thus detectably changing the behavior of said color center defects.

B10. The device of paragraph B9, wherein the said analyte-specific binding agents are aptamers or SOMAmers.

B11. The device of paragraph B9, wherein the said optical filter layer is comprised of layered dielectric films to form a dichroic bandpass filter.

B12. The device of paragraph B9, wherein the said detection layer is comprised of CMOS avalanche photodetectors in immediate contact with the said optical filter layer, wherein the signals from said photodetectors are passed through high-speed electronic gates, the signals that pass through said high-speed gates are passed to event counters, and the resulting data collected by the event counters are routed to a processor for analysis.

B13. The device of paragraph B9, in which a collection of said tethered SOMAmers are identical in their specificity for a specific analyte and interact in a measurable way with a collection of said nitrogen-vacancy centers which collectively emit fluorescent light captured by an individual photodetector.

B14. The device of paragraph B13, in which the said collection of SOMAmers consists of a single molecule, and the said collection of nitrogen-vacancy centers consists of a single center.

B15. The device of paragraph B13, in which the said collection of SOMAmers consists of a multiple molecules identically specific for the same analyte, and the said collection of nitrogen-vacancy centers consists of a single center.

B16. The device of paragraph B13, in which there are multiple said collections of tethered SOMAmers, each said collection being specific to a different analyte.

B17. The device of paragraph B16, in which the number of said collections of tethered SOMAmers is between 100 and 10,000.

B18. The device of paragraph B13, in which means are included to direct fluids to the fluid-contacting surface of the diamond layer, including means to recirculate said fluids if desired, said fluids to include:
  a) The sample fluid;
  b) Wash fluid used to remove molecules binding in non-specific fashion to the said SOMAmers or the said fluid-contacting surface of the diamond layer; and
  c) Regeneration fluid used to remove molecules binding in both specific and non-specific fashion to the said SOMAmers or the said fluid-contacting surface of the diamond layer without causing damage or denaturation to said SOMAmers or said fluid-contacting surface of the diamond layer.

B19. The device of paragraph B18, in which the said sample fluid is a biological fluid from a human subject.

B20. The device of paragraph B19, in which the said biological fluid is urine.

B21. The device of paragraph B20, in which the device is designed to be contained within a toilet, urinal, or other urine receptacle, thereby allowing the capture and analysis of urine from said toilet, urinal, or urine receptacle.

B22. The device of paragraph B21, in which the data generated by the device is compared with a proteomic database for diagnosis of possible disease states.

B23. The device of paragraph B18, in which analyte concentrations are measured in the said sample fluid according to the described method:
  a) Preparing multiple calibration samples of fluids containing known concentrations of the said analyte;
  b) Directing said calibration samples to the said fluid-contacting surface of the diamond layer and allowing the said analyte sufficient opportunity to bind to the said tethered SOMAmers, optionally including recirculation of said calibration sample fluid;
  c) Directing said wash fluid to the said fluid-contacting surface of the diamond layer, allowing the said wash fluid sufficient opportunity to remove molecules binding in non-specific fashion to the said SOMAmers, such opportunity optionally including recirculation of said wash fluid;
  d) Irradiating the said nitrogen-vacancy centers with excitation light, said light including frequencies that induce fluorescent emission of said nitrogen-vacancy centers, and measuring said fluorescent emission intensity;
  e) Irradiating the said nitrogen-vacancy centers with microwave radiation, the frequency of said microwave radiation being varied across a range that is expected to include resonant frequencies that induce conversion of ground state electrons in the said nitrogen-vacancy centers from the 0-spin state to the $\pm 1$-spin states;
  f) Generating plots for each said calibration sample of said fluorescent emission intensity versus said microwave radiation frequency;
  g) Generating a calibration curve of analyte concentration versus some chosen characteristic of the plots of said calibration samples from (f);
  h) Repeating steps (b) through (f), using samples of interest instead of calibration samples to generate plots as in (f); and
  i) Applying the said calibration curve of step (f) to determine the analyte concentration of each said sample of interest.

B24. The device and method of paragraph B23, in which the said chosen characteristic of the said plot is the resonant microwave frequency, determined by locating the most extreme local minimum.

B25. The device and method of paragraph B23, in which the said chosen characteristic of the said plot describes the width of the resonant inverted peak in some fashion, for instance the full-width-half-maximum (FWHM), or the coefficient of variation (CV).

B26. The device of paragraph B18, in which analyte concentrations are measured in the said sample fluid according to the described method:
  a) Preparing multiple calibration samples of fluids containing known concentrations of the said analyte;
  b) Directing said calibration samples to the said fluid-contacting surface of the diamond layer and allowing the said analyte sufficient opportunity to bind to the said tethered SOMAmers, optionally including recirculation of said calibration sample fluid;

c) Directing said wash fluid to the said fluid-contacting surface of the diamond layer, allowing the said wash fluid sufficient opportunity to remove molecules binding in non-specific fashion to the said SOMAmers, such opportunity optionally including recirculation of said wash fluid;

d) Irradiating the said nitrogen-vacancy centers with a series of square wave pulses, $p_i$, of excitation light, said light including frequencies that induce fluorescent emission of said nitrogen-vacancy centers, each said pulse of long enough duration to cause full polarization of the said nitrogen-vacancy centers into the 0-spin state. Further varying the spacing $T_1$ between these said excitation pulses $p_i$;

e) Measuring the fluorescent intensity immediately after the start of each said excitation pulse, as well as a reference intensity, taken towards the end of each said excitation pulse, said reference intensity to be measured when the spin states should be fully polarized to the 0-spin state;

f) Calculating normalized intensities by dividing the said fluorescent intensity at the start of each said excitation pulse $p_i$ with the corresponding said reference intensity;

g) Generating response plots for each of the said calibration samples, by plotting the said reference intensities for each said pulse $p_i$ against the said spacing time $T_1$ immediately preceding pulse $p_i$;

h) Finding the relaxation time $T_1$ for each said calibration sample by fitting a decaying exponential of the form $y=I_0*\exp(-\tau/T_1)$, where y is the dependent variable consisting of the collection of said normalized intensities for each said pulse $p_i$, and the independent variable T is the collection of said spacing times preceding each said pulse $p_i$;

i) Generating a calibration curve of known analyte concentration in the said calibration samples versus relaxation time $T_1$ from step (h);

j) Repeating steps (b) through (h), using samples of interest instead of calibration samples to generate plots as in (g) and finding relaxation times as in step (h); and k) Applying the said calibration curve of step (i) to determine the analyte concentration of each said sample of interest.

C. A device for detecting target molecules, comprising:
a surface configured to contact a fluid;
a plurality of capture reagents attached to the surface, each capture reagent configured to bind to a target molecule;
a plurality of color centers located proximate the surface; and
at least one detector configured to detect a change in a property of at least one of the color centers in response to binding the target molecule to one of the capture reagents.

C1. The device of paragraph C, wherein the target molecule is a protein, and the capture reagents are aptamers.

C2. The device of paragraph C1, wherein the aptamers are nucleic acid molecules.

C3. The device of paragraph C2, wherein the nucleic acid molecules have at least one 5-position modified pyrimidine.

C4. The device of paragraph C, wherein the surface is a surface of a diamond crystal, and the color centers are nitrogen-vacancy centers of the diamond crystal.

C5. The device of paragraph C4, wherein the diamond crystal is a single-crystal diamond.

C6. The device of paragraph C4, further comprising an optical source configured to irradiate the nitrogen-vacancy centers with radiation having a first range of wavelengths, and wherein the detector is configured to detect radiation having a second range of wavelengths.

C7. The device of paragraph C4, wherein the property is associated with a magnetic resonance of the nitrogen vacancy centers.

C8. The device of paragraph C4, further comprising a microwave source configured to provide microwave radiation having a range of frequencies including a resonant frequency of sublevels of an electronic ground state of the nitrogen vacancy centers.

C9. The device of paragraph C, wherein capture reagents includes reagents belonging to a plurality of capture species, and each capture species is configured to bind to target molecules of a particular target species.

C10. A device for measuring a concentration of target molecules, comprising:
a crystalline film including at least one color center;
a plurality of capture reagents attached to a surface of the crystalline film and configured to bind to a target molecule; and
a detector assembly configured to irradiate the color center with excitation light and to detect emission of electromagnetic radiation from the color center.

C11. The device of paragraph C10, wherein the capture reagents include a magnetic spin label, and a magnetic field at the color center changes in response to binding the target molecule to one of the capture reagents.

C12. The device of paragraph C11, wherein the detector assembly is configured to irradiate the color center with microwave radiation having a frequency capable of inducing conversion of ground-state electrons in the color center from a first sub-state to a second sub-state.

C13. The device of paragraph C10, wherein the crystalline film is a diamond film, and the color center is a nitrogen vacancy center.

C14. The device of paragraph C10, wherein binding of one of the capture reagents to one of the target molecules produces a detectable change in the emission of electromagnetic radiation from the color center by changing an interaction between a spin label of the capture reagent and the color center.

C15. A device for detecting target molecules, comprising:
a plurality of capture reagents attached to a surface of a crystalline substrate and configured to capture target molecules from a sample fluid;
a plurality of color centers disposed at fixed distances from the capture reagents, the fixed distances being sufficiently small that a property of at least one of the color centers changes in response to capture of one of the target molecules by one of the capture reagents; and
a detector configured to detect a change in the property of at least one of the color centers.

C16. The device of paragraph C15, wherein the capture reagents are aptamers.

C17. The device of paragraph C16, wherein the capture reagents are oligonucleotides.

C18. The device of paragraph C16, wherein the capture reagents are nucleic acid molecules having at least one 5-position modified pyrimidine.

C19. The device of paragraph C18, wherein the crystalline substrate is a diamond film, and the color centers are nitrogen vacancy centers.

D0. A method for detecting target molecules in a sample fluid, the method comprising:
contacting, with a sample fluid, a capture reagent attached to a surface and configured to bind to a target molecule;
irradiating a color center disposed proximate the surface with excitation light configured to induce fluorescent emission by the color center;
measuring an intensity of the fluorescent emission using one or more detectors; and
detecting a change in the intensity of the fluorescent emission in response to binding the target molecule to the capture reagent.

D1. The method of D0, further comprising:
irradiating the color center with microwave radiation at a frequency capable of inducing conversion of ground-state electrons in the color center from a first sub-state to a second sub-state; and
wherein detecting a change in the intensity of the fluorescent emission in response to binding the target molecule to the capture reagent includes identifying resonance behavior of the color center based on a relationship between the measured intensity of the fluorescent emission and the frequency of the microwave radiation.

D2. The method of paragraph D0 or D1, wherein the target molecule is a protein.

D3. The method of any of paragraphs D0-D2, wherein the capture reagents are aptamers.

D4. The method of any of paragraphs D0-D3, wherein the capture reagents are nucleic acid molecules having at least one 5-position modified pyrimidine.

D5. The method of any of paragraphs D0-D4, wherein the surface is a surface of a diamond crystal, and the color centers are nitrogen-vacancy centers of the diamond crystal.

D6. The method of any of paragraphs D0-D5, wherein the capture reagents are aptamers including at least one first 5-position modified pyrimidine and at least one second 5-position modified pyrimidine, wherein the first 5-position modified pyrimidine and the second 5-position modified pyrimidine are different 5-position modified pyrimidines;
wherein the first 5-position modified pyrimidine is a 5-position modified uridine and
wherein the second 5-position modified pyrimidine is a 5-position modified cytidine; or
wherein the first 5-position modified pyrimidine is a 5-position modified cytidine and
wherein the second 5-position modified pyrimidine is a 5-position modified uridine.

E0. A method for measuring a concentration of target molecules, comprising:
exposing a fluid to a surface of a crystalline film to allow capture reagents attached to the surface to bind to target molecules within the fluid;
irradiating the film with excitation light configured to induce fluorescent emission by at least one color center within the crystalline film;
detecting, based on the fluorescent emission, a change in a property of the color center in response to binding between the target molecules and the capture reagents; and
determining, based on the detected change, a concentration of target molecules within the fluid.

E1. The method of paragraph E0, wherein the target molecules are proteins.

E2. The method of paragraph E1 or E2, wherein the capture reagents include a magnetic spin label, and a magnetic field at the at least one color center changes in response to binding between the target molecules and the capture reagents.

E3. The method of any of paragraphs E0-E2, wherein irradiating the film with excitation light includes irradiating the color center with microwave radiation having a frequency capable of inducing conversion of ground-state electrons in the color center from a first sub-state to a second sub-state.

E4. The method of any of paragraphs E0-E3, wherein the color center is a nitrogen vacancy center.

E5. The method of any of paragraphs E0-E4, wherein the crystalline film is a diamond film.

F0. A method for detecting target molecules comprising:
exposing a crystalline substrate to a sample fluid such that a plurality of capture reagents attached to a surface of the crystalline substrate bind to target molecules within the sample fluid; and
identifying a change in a property of one or more color centers within the crystalline substrate in response to binding the target molecules to the capture reagents.

F1. The method of paragraph F0, wherein the crystalline substrate is a diamond film, and the color centers are nitrogen vacancy centers within the diamond film.

F2. The method of paragraph F0 or F1, further comprising irradiating the crystalline substrate with electromagnetic radiation, and wherein identifying a change in a property of one or more color centers includes detecting fluorescent radiation emitted by the color centers.

F3. The method of any of paragraphs F0-F2, wherein the capture reagents are aptamers including at least two distinct 5-position modified pyrimidine.

F4. The method of any of paragraphs F0-F3, wherein the target molecules are proteins.

G0. A method for manufacturing a device for detecting the presence of protein molecules in a sample fluid, comprising:
fabricating a crystalline film;
embedding a plurality of substitute atoms within the crystalline film;
creating a plurality of vacancies within the crystalline film;
creating color centers within the crystalline film by collocating at least some of the substitute atoms with at least some of the vacancies;
attaching a plurality of capture reagents to a first surface of the crystalline film; and
attaching a layer of photodetectors to a second surface of the crystalline film.

G1. The method of paragraph G0, wherein the crystalline film is fabricated using chemical vapor deposition.

G2. The method of paragraph G0 or G1, wherein the vacancies are created using an electron beam.

G3. The method of any of paragraphs G0-G2, wherein the substitute atoms are collocated with the vacancies by annealing the crystalline film at a high temperature.

G4. The method of any of paragraphs G0-G3, wherein attaching the layer of photodetectors includes fabricating the layer of photodetectors using lithography and adhering the layer of photodetectors to the second surface of the crystalline film using optically transparent adhesive.

What is claimed is:
1. A device for detecting label-free target analytes, comprising:

a surface configured to contact a fluid;

at least two capture reagents attached to the surface, the at least two capture reagents being configured to bind to different label-free target analytes respectively;

a plurality of color centers located proximate the surface; and at least one detector configured to detect a change in a property of at least one of the color centers in response to binding one of the different label-free target analytes to a corresponding one of the capture reagents;

wherein the capture reagents are aptamers each having a negatively charged backbone.

2. The device of claim 1, wherein the at least one detector is configured to detect the change in the property by sensing fluorescence emitted by the at least one color center.

3. The device of claim 1, wherein the label-free target analytes are proteins and the proteins are charged.

4. The device of claim 1, wherein binding one of the different label-free target analytes to the corresponding one of the capture reagents forms a complex, and the change in the property of the at least one color center is associated with a charge distribution of the complex.

5. The device of claim 1, wherein the surface is the surface of a diamond crystal and the color centers are nitrogen-vacancy centers of the diamond crystal.

6. A device for detecting label-free target molecules, comprising:

at least two capture reagents attached to a surface, wherein each of the at least two capture reagents is configured to bind to a different label-free target molecule to form a complex including at least the capture reagent and the label-free target molecule;

one or more color centers disposed proximate the surface such that forming the complex causes a change in an electric field at one or more of the color centers; and a detector configured to detect the change in the electric field at the one or more of the color centers.

7. The device of claim 6, wherein the capture reagents are configured to attract positive ions and the complex includes at least one positive ion.

8. The device of claim 7, wherein the capture reagents are aptamers having negatively charged backbones.

9. The device of claim 6, wherein the detector is configured to detect the change in the electric field by sensing radiation emitted by the one or more of the color centers.

10. The device of claim 9, further comprising an optical source configured to excite the one or more of the color centers with excitation light.

11. The device of claim 6, wherein the surface is a surface of a diamond substrate and the color centers are nitrogen-vacancy centers.

12. A device for detecting label-free target molecules, comprising:

a color center disposed in a substrate;

a capture reagent attached to a surface of the substrate, wherein the capture reagent is configured to attract positive ions from a solution and to capture a label-free target molecule from the solution, and wherein a change in charge distribution associated with attracting one or more of the positive ions and capturing the label-free target molecule by the capture reagent causes a change in a property of the color center; and a detector configured to detect the change in the property of the color center.

13. The device of claim 12, wherein the substrate comprises diamond and the color center is a nitrogen-vacancy center.

14. The device of claim 12, wherein the change in the property of the color center corresponds to a change in an electric field local to the color center.

15. The device of claim 12, wherein the detector is configured to detect the change in the property of the color center by detecting fluorescence emitted from the color center.

16. The device of claim 15, further comprising an optical source configured to excite the color center to emit the fluorescence.

17. The device of claim 12, wherein the capture reagent is an aptamer having a negatively charged backbone.

18. The device of claim 17, wherein the aptamer has at least one 5-position modified pyrimidine.

19. The device of claim 12, wherein the label-free target molecule is a protein.

20. The device of claim 12, wherein the capture reagent is a first capture reagent and the label-free target molecule is a first label-free target molecule, the device further comprising a second capture reagent attached to the surface and configured to attract a second label-free target molecule, wherein the first and second label-free target molecules are different types of molecules.

* * * * *